US012685713B2

(12) United States Patent
Komorowski et al.

(10) Patent No.: US 12,685,713 B2
(45) Date of Patent: Jul. 21, 2026

(54) GLP-1R AGONIST AND DPP-4 INHIBITOR COMPOSITIONS AND METHODS OF USING

(71) Applicant: JDS Therapeutics, LLC, Harrison, NY (US)

(72) Inventors: James R. Komorowski, Trumbull, CT (US); Devon Bernsley, New York, NY (US); Sophia Ramirez, Marietta, GA (US)

(73) Assignee: JDS Therapeutics, LLC, Harrison, NY (US)

( * ) Notice: Subject to any disclaimer, the term of this patent is extended or adjusted under 35 U.S.C. 154(b) by 0 days.

(21) Appl. No.: 18/652,734

(22) Filed: May 1, 2024

(65) Prior Publication Data

US 2024/0366525 A1 Nov. 7, 2024

Related U.S. Application Data

(60) Provisional application No. 63/463,191, filed on May 1, 2023.

(51) Int. Cl.
| | |
|---|---|
| *A61K 31/05* | (2006.01) |
| *A61K 31/12* | (2006.01) |
| *A61K 31/4375* | (2006.01) |
| *A61K 36/258* | (2006.01) |

(52) U.S. Cl.
CPC .............. *A61K 31/05* (2013.01); *A61K 31/12* (2013.01); *A61K 31/4375* (2013.01); *A61K 36/258* (2013.01)

(58) Field of Classification Search
None
See application file for complete search history.

(56) References Cited

U.S. PATENT DOCUMENTS

| | | |
|---|---|---|
| 2018/0105498 A1 | 4/2018 | Zemel et al. |
| 2020/0338016 A1* | 10/2020 | Fenzl ..................... A61K 8/347 |
| 2024/0366525 A1 | 11/2024 | Komorowski et al. |

FOREIGN PATENT DOCUMENTS

WO 2021/202245 A1 10/2021

OTHER PUBLICATIONS

Sugier et al., Molecules, 2021, 26, 7692, 1-22 pages.*
Abe, "Timing of Medium-Chain Triglyceride Consumption Modulates Effects in Mice with Obesity Induced by a High-Fat High-Sucrose Diet," Nutrients, 2022; 14(23):5096.
Abiola et al., "Potential Role of Phytochemicals as Glucagon-like Peptide 1 Receptor (GLP-1R) Agonists in the Treatment of Diabetes Mellitus," Pharmaceuticals, 2024; 17(6):736.
Aguayo-Guerrero et al., "Sucralose: From Sweet Success to Metabolic Controversies—Unraveling the Global Health Implications of a Pervasive Non-Caloric Artificial Sweetener," Life, 2024; 14(3):323.
Ahmad et al., "Effect of sucralose and aspartame on glucose metabolism and gut hormones," Nutrition Reviews, 2020; 78(9): pp. 725-746.
Alfaris et al., "GLP-1 single, dual, and triple receptor agonists for treating type 2 diabetes and obesity: a narrative review," Lancet, 2024; 75: pp. 1-21.
Alli-Oluwafuyi et al., "Curcumin induces secretion of glucagon-like peptide-1 through an oxidation-dependent mechanism," Biochimie, 2019; 165: pp. 250-257.
Alshammaa et al., "The metabolic effect of medicinal plants and synthetic anti-obesity products on human health," Horizon, 2024; 11(3): pp. 704-718.
Anand et al., "Chapter 8, Dietary Fatty Acids, Gut Microbiome, and Gut-Brain Communication: A Current Perspective," Singapore: Springer Nature, 2022: pp. 121-138.
Anghel et al., "Novel luciferase-based glucagon-like peptide 1 reporter assay reveals naturally occurring secretagogues," British Journal of Pharmacology, 2022; 179(19): pp. 4738-4753.
Ansari et al., "Antidiabetic actions of ethanol extract of *Camellia sinensis* leaf ameliorates insulin secretion, inhibits the DPP-IV enzyme, improves glucose tolerance, and increases active GLP-1 (7-36) levels in high-fat-diet-fed rats," Medicines, 2022; 9(11):56.
Ansari et al., "Anti-hyperglycaemic and insulin-releasing effects of *Camellia sinensis* leaves and isolation characterisation of active compounds," British Journal of Nutrition, 2021; 126(8): pp. 1149-1163.
Ansari et al., "Therapeutic Potential of Quercetin in the Management of Type-2 Diabetes Mellitus," Life, 2022; 12(8):1146.
Apalowo et al., "Nutritional Characteristics, Health Impact, and Applications of Kefir," Foods, 2024; 13(7):1026.
Bai et al., "Curcumin alone not combined with piperine exerts cardioprotective effects in pressure-overload rats by increasing glucagon-like peptide-1 receptor signaling and additional properties," Journal of Traditional and Complementary Medi-cine, 2024.
Baskaran et al., "TRPV1 activation counters diet-induced obesity through sirtuin-1 activation and PRDM-16 deacetylation in brown adipose tissue," International Journal of Obesity, 2017; 41(5): pp. 739-749.
Batsis et al., "A Systematic Review of Dietary Supplements and Alternative Therapies for Weight Loss," Obesity, 2021; 29(7): pp. 1102-1113.
Bengoa et al., "Exopolysaccharides from Lactobacillus paracasei isolated from kefir as potential bioactive compounds for microbiota modulation," Frontiers in Microbiology, 2020; 11:583254.
Bhaswant et al., "Mechanisms of enhanced insulin secretion and sensitivity with n-3 unsaturated fatty acids," The Journal of Nutritional Biochemistry, 2015; 26(6): pp. 571-584.

(Continued)

*Primary Examiner* — Michael V Meller

(74) *Attorney, Agent, or Firm* — Arnall Golden Gregory LLP

(57) ABSTRACT

Disclosed herein are compositions comprising a GLP-1R agonist composition, a DPP-4 inhibitor composition, or a combination of both. The description contained herein describes methods for inducing weight loss and/or boosting satiety in a subject. The compositions described herein may be formulated for oral administration, and in some embodiments, may further comprise enteric or pH-responsive coatings.

9 Claims, No Drawings

(56) References Cited

OTHER PUBLICATIONS

Borah et al., "Phytomedicine as a source of SGLT2 inhibitors, GLP-1 secretagogues and DPP-IV inhibitors for mitigation of Diabetic Nephropathy," Phytomedicine Plus, 2022; 2(2):100225.

Brown et al., "Ingestion of diet soda before a glucose load augments glucagon-like peptide-1 secretion," Diabetes Care, 2009; 32(12): pp. 2184-2186.

Cai et al., "Hypoglycemic benefit and potential mechanism of a polysaccharide from Hericium erinaceus in streptozotoxin-induced diabetic rats," Process Biochemistry, 2020; 88: pp. 180-188.

Chakraborty et al., "Edible mushrooms: An emerging therapeutic of diabetes," The Thai Journal of Pharmaceutical Sciences, 2022; 46(4): pp. 373-384.

Chen et al., "Review of Ginseng Anti-Diabetic Studies," Molecules, 2019; 24(24):4501.

Dirksen et al., "Energy intake, gastrointestinal transit, and gut hormone release in response to oral triglycerides and fatty acids in men with and without severe obesity," Am J Physiol Gastrointest Liver Physiol, 2019; 316(3):G332-G337.

Ebrahimi et al., "Effect and mechanism of herbal ingredients in improving diabetes mellitus complications," Jundishapur J Nat Pharm Prod., 2017; 12(1):e31657.

El-Gohary et al., "Novel insights into the augmented effect of curcumin and liraglutide in ameliorating cisplatin-induced nephrotoxicity in rats: Effects on oxidative stress, inflammation, apoptosis and pyroptosis via GSK-3β," Archives of Biochemistry and Biophysics, 2023; 749:109801.

Eraky et al., "Antidiabetic effects of quercetin and liraglutide combination through modulation of TXNIP/IRS-1/PI3K pathway," Cell Biochemistry and Function, 2022; 40(1): pp. 90-102.

Feltrin et al., "Effects of intraduodenal fatty acids on appetite, antropyloroduodenal motility, and plasma CCK and GLP-1 in humans vary with their chain length," Am J Physiol Regul Integr Comp Physiol, 2004; 287(3): pp. R524-R33.

Fontes et al., "Mushrooms on the plate: Trends towards NAFLD treatment, health improvement and sustainable diets," European Journal of Clinical Investigation, 2022; 52:e13667.

Friedman, "Mushroom Polysaccharides: Chemistry and Antiobesity, Antidiabetes, Anticancer, and Antibiotic Properties in Cells, Rodents, and Humans," Foods, 2016; 5(4):80.

Gaballah et al., "Mechanistic insights into the effects of quercetin and/or GLP-1 analogue liraglutide on high-fat diet/streptozotocin-induced type 2 diabetes in rats," Biomedicine & Pharmacotherapy, 2017; 92: pp. 331-339.

Geraedts et al., "Different tastants and low-caloric sweeteners induce differential effects on the release of satiety hormones," Food Chem, 2011; 129(3): pp. 731-738.

Go et al., "GLP-1 and its derived peptides mediate pain relief through direct TRPV1 inhibition without affecting thermoregulation," Experimental & Molecular Medicine, 2024.

Grotz et al., "A 12-week randomized clinical trial investigating the potential for sucralose to affect glucose homeostasis," Regulatory Toxicology and Pharmacology, 2017; 88: 22-33.

Hadisaputro et al., "The Effects of Oral Plain Kefir Supplementation on Proinflammatory Cytokine Properties of the Hyper-glycemia Wistar Rats Induced by Streptozotocin," Acta medica Indonesiana, 2012; 44: pp. 100-104.

Haneishi et al., "Polyunsaturated fatty acids-rich dietary lipid prevents high fat diet-induced obesity in mice," Scientific Reports, 2023; 13(1):5556.

He et al., "Progress in the discovery of naturally occurring antidiabetic drugs and in the identification of their molecular targets," Fitoterapia, 2019; 134: pp. 270-289.

He, "Examination of the Ginseng Utility from the Perspective of the Nutrition Professional," Mount Saint Vincent University, 2018.

Hui et al., "Capsaicin improves glucose homeostasis by enhancing glucagon-like peptide-1 secretion through the regulation of bile acid metabolism via the remodeling of the gut microbiota in male mice," The FASEB Journal, 2020; 34(6): pp. 8558-8573.

Ibrahim et al., "Dietary conjugated linoleic acid and medium-chain triglycerides for obesity management," Journal of Biosciences, 2021; 46(1).

Imeryuz et al., "Glucagon-like peptide-1 inhibits gastric emptying via vagal afferent-mediated central mechanisms," Am J Physiol, 1997; 273(4): pp. G920-G927.

International Search Report and Written Opinion issued in PCT/US2024/027307, mailed Sep. 23, 2024.

International Search Report and Written Opinion issued in PCT/US2024/057908, mailed Mar. 26, 2025.

Ismail et al., "Novel strategies in the oral delivery of antidiabetic peptide drugs—Insulin, GLP 1 and its analogs," Eur. J. Pharm. Biopharm., 2017; 115: pp. 257-267.

Jang et al., "Gut-expressed gustducin and taste receptors regulate secretion of glucagon-like peptide-1," Proc Natl Acad Sci U S A., 2007; 104(38): pp. 15069-74.

Jiang et al., "Therapeutic potential of berberine against neurodegenerative diseases," Science China Life Sciences, 2015; 58: pp. 564-569.

Kato et al., "Curcumin improves glucose tolerance via stimulation of glucagon-like peptide-1 secretion," Molecular Nutrition & Food Research, 2017; 61(3):1600471.

Kato, "Bioactive compounds in plant materials for the prevention of diabetes and obesity," Bioscience, Biotechnology, and Biochemistry, 2019; 83(6): pp. 975-985.

Kim et al., "Anti-obesity effects of cultivated ginseng,-wild simulated ginseng and-red ginseng extracts," Herbal Formula Science, 2019; 27(4): pp. 269-284. (English abstract provided).

Kim et al., "Medicinal plants qua glucagon-like peptide-1 secretagogue via intestinal nutrient sensors," Evidence-based Complementary and Alternative Medicine, 2015; 2015(1):171742.

Berge et al., "Pharmaceutical Salts," J. Pharm. Sci., 1977, 66(1): pp. 1-19.

Kim et al., "The aglycone of ginsenoside Rg3 enables glucagon-like peptide-1 secretion in enteroendocrine cells and alleviates hyperglycemia in type 2 diabetic mice", Sci Rep. 2015; 5(18325): 12 pages. Available at: <URL: https://doi.org/10.1038/srep18325>.

U.S. Department of Health & Human Services, Food & Drug Administration, "Guidance for Industry: Q3C Impurities: Residual Solvents," Dec. 1997, [online]. Retrieved from the Internet: <URL: https://www.fda.gov/downloads/drugs/guidances/ucm073394.pdf>.

PCT/US2024/027307, May 1, 2024, James R. Komorowski et al.

PCT/US2024/057908, Nov. 27, 2024, James R. Komorowski et al.

U.S. Appl. No. 63/463,191, filed May 1, 2023, James R. Komorowski et al.

U.S. Appl. No. 18/963,411, filed Nov. 27, 2024, James R. Komorowski et al.

Kong, "Effects of kefirs on glycemic, insulinemic and satiety responses," A thesis submitted to graduate faculty, Iowa State University, 2009.

Koole et al., "Allosteric Ligands of the Glucagon-Like Peptide 1 Receptor (GLP-1R) Differentially Modulate Endogenous and Exogenous Peptide Responses in a Pathway-Selective Manner: Implications for Drug Screening," Molecular Pharmacology, 2010; 78(3): pp. 456-465.

Korkmaz et al., "The comparison of the antidiabetic effects of exenatide, empagliflozin, quercetin, and combination of the drugs in type 2 diabetic rats," Fundamental & Clinical Pharmacology, 2024; 38(3): pp. 511-522.

Lai et al., "Chinese herbal medicine decreases incidence of hepatocellular carcinoma in diabetes mellitus patients with regular insulin management," World J Gastrointest Oncol, 2024; 16(3): pp. 716-731.

Lakhanpal et al., "Medicinal and nutraceutical genetic resources of mushrooms," Plant Genetic Resources, 2005; 3(2): pp. 288-303.

Lee et al., "Combination of Lacticaseibacillus paracasei BEPC22 and Lactiplantibacillus plantarum BELP53 attenuates fat accumulation and alters the metabolome and gut microbiota in mice with high-fat diet-induced obesity," Food & Function, 2024; 15(2): pp. 647-662.

Lee et al., "Natural products and body weight control," N Am J Med Sci, 2011; 3(1): pp. 13-19.

(56) References Cited

OTHER PUBLICATIONS

Lertrit et al., "Effects of sucralose on insulin and glucagon-like peptide-1 secretion in healthy subjects: a randomized, double-blind, placebo-controlled trial," Nutrition, 2018; 55-56: pp. 125-130.

Li et al., "Role of dietary edible mushrooms in the modulation of gut microbiota," Journal of Functional Foods, 2021; 83:104538.

Liu et al., "Angelica acutiloba Root Attenuates Insulin Resistance Induced by High-Fructose Diet in Rats," Phytotherapy Research, 2011; 25(9): pp. 1283-1293.

Liu et al., "Association of GLP-1 secretion with anti-hyperlipidemic effect of ginsenosides in high-fat diet fed rats," Metabolism: clinical and experimental, 2014; 63(10): pp. 1342-1351.

Liu et al., "Effects of Green Tea Extract on Insulin Resistance and Glucagon-Like Peptide 1 in Patients with Type 2 Diabetes and Lipid Abnormalities: A Randomized, Double-Blinded, and Placebo-Controlled Trial," PLOS One, 2014; 9(3):e91163.

Liu et al., "Mushroom polysaccharides with potential in anti-diabetes: Biological mechanisms, extraction, and future perspectives: A review," Frontiers in Nutrition, 2022; 9:1087826.

Liu et al., "The structures of two polysaccharides from Angelica sinensis and their effects on hepatic insulin resistance through blocking RAGE," Carbohydrate Polymers, 2022; 280: 119001.

Lu et al., "An updated patent review of GLP-1 receptor agonists (2020-present)," Expert Opinion on Therapeutic Patents, 2023; 33(9): pp. 597-612.

Lupien-Meilleur et al., "Interplay Between Gut Microbiota and Gastrointestinal Peptides: Potential Outcomes on the Regulation of Glucose Control," Canadian Journal of Diabetes, 2020; 44(4): pp. 359-367.

Ma et al., "Effect of the artificial sweetener, sucralose, on gastric emptying and incretin hormone release in healthy subjects," Am J Physiol Gastrointest Liver Physiol, 2009; 296(4): pp. G735-739.

Maher et al., "A comparison of the satiating properties of medium-chain triglycerides and conjugated linoleic acid in participants with healthy weight and overweight or obesity," European Journal of Nutrition, 2021; 60(1): pp. 203-215.

Maher et al., "A systematic review and meta-analysis of medium-chain triglycerides effects on acute satiety and food intake," Critical Reviews in Food Science and Nutrition, 2021; 61 (4): pp. 636-648.

Maher, "An exploration of lipids with the potential to influence appetite and food intake," Oxford Brookes University—thesis, 2019.

Mansour et al., "Nutrients related to GLP1 secretory responses," Nutrition, 2013; 29(6): pp. 813-820.

Martel et al., "Anti-obesogenic and antidiabetic effects of plants and mushrooms," Nature Reviews Endocrinology, 2017; 13(3): pp. 149-160.

McCarty et al., "Capsaicin may have important potential for promoting vascular and metabolic health," Open Heart, 2015; 2(1):e000262.

Mohankumar et al., "Dietary conjugated linoleic acid isomers (cis-9, trans-11 and trans-10, cis-12) modulate insulin-dependent and independent skeletal muscle glucose transport in vitro," Canadian Journal of Diabetes, 2009; 33(3):219. (abstract only).

Moore et al., "GLP-1 Agonists for Weight Loss: Pharmacology and Clinical Implications," Adv. Ther., 2023; 40(3): pp. 723-742.

Naughton et al., "The Acute Effect of Oleic- or Linoleic Acid-Containing Meals on Appetite and Metabolic Markers; A Pilot Study in Overweight or Obese Individuals," Nutrients, 2018; 10(10):1376.

Niego et al., "Macrofungi as a nutraceutical source: Promising bioactive compounds and market value," J Fungi, 2021; 7: 397.

Nonaka et al., "Dietary medium-chain triglyceride decanoate affects glucose homeostasis through GPR84-mediated GLP-1 secretion in mice," Frontiers in Nutrition, 2022; 9:848450.

Pan et al., "Antiobesity molecular mechanisms of action: Resveratrol and pterostilbene," BioFactors, 2018; 44(1): pp. 50-60.

Panchal et al., "Capsaicin in Metabolic Syndrome," Nutrients, 2018; 10(5):630.

Patyra et al., "Pharmacological and phytochemical insights on the pancreatic ß-cell modulation by Angelica L. roots," Journal of Ethnopharmacology, 2024; 329:118133.

Patyra, "Effects and underlying mechanism of plant secondary metabolites on insulin secretion regulation," Université de Montpellier Medical University of Warsaw (Pologne), 2023.

Peluzio et al., "Kefir and Intestinal Microbiota Modulation: Implications in Human Health," Frontiers in Nutrition, 2021; 8.

Peng et al., "Hypoglycemic effects and associated mechanisms of resveratrol and related stilbenes in diet," Food & Function, 2024; 15(5): pp. 2381-2405.

Planes-Muñoz et al., "In vitro effect of green tea and turmeric extracts on GLP-1 and CCK secretion: the effect of gastrointestinal digestion," Food & function, 2018; 9(10):5245-50.

Rai et al., "Therapeutic applications of mushrooms and their biomolecules along with a glimpse of in silico approach in neurodegenerative diseases," Biomedicine & Pharmacotherapy, 2021; 137:111377.

Rai, "Medicinal mushrooms," Advances in mushroom biology and production. Mushroom Society of India, NRCM, Solan, Chambaghat, HP, 1997: pp. 355-368.

Raoof et al., "Chapter 10—Natural Products for the Management of Diabetes," In Atta_ur_Rahman A. ed., Studies in Natural Products Chemistry: Elsevier, 2018; (59): pp. 323-374.

Raskin et al., "Can an Apple a Day Keep the Doctor Away?" Current Pharmaceutical Design, 2004; 10: pp. 3419-3429.

Reidelberger et al., "Role of capsaicin-sensitive peripheral sensory neurons in anorexic responses to intravenous infusions of cholecystokinin, peptide YY-(3-36), and glucagon-like peptide-1 in rats," American Journal of Physiology-Endocrinology and Metabolism, 2014; 307(8): pp. E619-E29.

Ren et al., "Rhamnogalacturonan-I enriched pectin from steamed ginseng ameliorates lipid metabolism in type 2 diabetic rats via gut microbiota and AMPK pathway," Journal of Ethnopharmacology, 2023; 301:115862.

Revilla et al., "Comparison of Several Procedures Used for the Extraction of Anthocyanins from Red Grapes," J. Agric. Food Chem., 1998; 46(11): pp. 4592-4597.

Servida et al., "Curcumin and Gut Microbiota: A Narrative Overview with Focus on Glycemic Control," International Journal of Molecular Sciences, 2024; 25(14):7710.

Shazmeen et al., "Role of stilbenes against insulin resistance: A review," Food Science & Nutrition, 2021; 9(11): pp. 6389-6405.

Shi et al., "Sweet Taste Receptor Expression and Its Activation by Sucralose to Regulate Glucose Absorption in Mouse Duodenum," Journal of food science, 2021; 86(2): pp. 540-545.

Smeets et al., "The acute effects of a lunch containing capsaicin on energy and substrate utilisation, hormones, and satiety," European Journal of Nutrition, 2009; 48(4): pp. 229-234.

Song et al., "Dietary Capsaicin Improves Glucose Homeostasis and Alters the Gut Microbiota in Obese Diabetic ob/ob Mice," Frontiers in Physiology, 2017; 8.

St-Onge et al., "Impact of medium and long chain triglycerides consumption on appetite and food intake in overweight men," Eur J Clin Nutr, 2014; 68(10): pp. 1134-1140.

Subramoniam, "Plants with anti-diabetes mellitus properties," CRC Press, 2016.

Sun et al., "Antidiabetic effects of pterostilbene through PI3K/Akt signal pathway in high fat diet and STZ-induced diabetic rats," Eur. J. Pharmacol., 2019; 859: 172526 (8 pages).

Talib et al., "Anti-Diabetic Effect of Lactobacillus Paracasei Isolated from Malaysian Water Kefir Grains," Probiotics and Antimicrobial Proteins, 2024; 16(6): pp. 2161-2180.

Tallarida, "Quantitative Methods for Assessing Drug Synergism," Genes & Cancer, 2011; 2(11): pp. 1003-1008.

Tan et al., "Quercetin Ameliorates Insulin Resistance and Restores Gut Microbiome in Mice on High-Fat Diets," Antioxidants, 2021; 10(8):1251.

Temizkan et al., "Sucralose enhances GLP-1 release and lowers blood glucose in the presence of carbohydrate in healthy subjects but not in patients with type 2 diabetes," Eur J Clin Nutr, 2015; 69(2): pp. 162-166.

(56) References Cited

OTHER PUBLICATIONS

Tian et al., "Curcumin Compensates GLP-1 Deficiency via the Microbiota-Bile Acids Axis and Modulation in Functional Crosstalk between TGR5 and FXR in ob/ob Mice," Molecular Nutrition & Food Research, 2023; 67(22):2300195.

Trakooncharoenvit et al., "Combination of alpha-Glycosyl-Isoquercitrin and Soybean Fiber Promotes Quercetin Bioavailability and Glucagon-like Peptide-1 Secretion and Improves Glucose Homeostasis in Rats Fed a High-Fat High-Sucrose Diet," Journal of Agricultural and Food Chemistry, 2021; 69(21): pp. 5907-5916.

Trujillo et al., "GLP-1 receptor agonists: a review of head-to-head clinical studies," Ther. Adv. Endocrinol. Metabol., 2015; 6(1): pp. 19-28.

Tsuda, "Possible abilities of dietary factors to prevent and treat diabetes via the stimulation of glucagon-like peptide-1 secretion," Molecular Nutrition & Food Research, 2015; 59(7): pp. 1264-1273.

Vieira et al., "Bioactive Compounds from Kefir and Their Potential Benefits on Health: A Systematic Review and Meta-Analysis," Oxidative Medicine and Cellular Longevity, 2021; 2021(1): pp. 1-34.

Wang et al., "Review Article Advances in Chinese herbal medicine for the treatment of diabetes," Int J Clin Exp Med, 2017; 10(9): pp. 13025-13036.

Wang et al., "Reviews of medium- and long-chain triglyceride with respect to nutritional benefits and digestion and absorption behavior," Food Research International, 2022; 155:111058.

Wang et al., "Silibinin improves L-cell mass and function through an estrogen receptor-mediated antioxidative mechanism," Phytomedicine, 2022; 99:154022.

Watanabe et al., "Applications of Medium-Chain Triglycerides in Foods," Frontiers in Nutrition, 2022; 9:802805.

Wei et al., "Selecting probiotics with the abilities of enhancing GLP-1 to mitigate the progression of type 1 diabetes in vitro and in vivo," Journal of Functional Foods, 2015; 18: pp. 473-486.

Wilson et al., "Methoxylation enhances stilbene bioactivity in Caenorhabditis elegans," BMC Pharmacology, 2008; 8(1):15.

Wolosowicz et al., "Recent Advances in the Treatment of Insulin Resistance Targeting Molecular and Metabolic Pathways: Fighting a Losing Battle?" Medicina, 2022; 58(4):472.

Wootten et al., "Modulation of the glucagon-like peptide-1 receptor signaling by naturally occurring and synthetic flavonoids," Journal of Pharmacology and Experimental Therapeutics, 2011; 336(2): pp. 540-550.

Wu et al., "Conjugated Linoleic Acid Ameliorates High Fat-Induced Insulin Resistance via Regulating Gut Microbiota-Host Metabolic and Immunomodulatory Interactions," Nutrients, 2024; 16(8):1133.

Wu et al., "Pharmacological effects of Radix Angelica Sinensis (Danggui) on cerebral infarction," Chinese Medicine, 2011; 6: pp. 1-5.

Yaribeygi et al., "Boosting GLP-1 by Natural Products," In: Sahebkar A, Sathyapalan T, eds. Natural Products and Human Diseases: Pharmacology, Molecular Targets, and Therapeutic Benefits, Cham: Springer International Publishing, 2021: pp. 513-522.

Yin et al., "Ginseng extract improves pancreatic islet injury and promotes ß-cell regeneration in T2DM mice," Frontiers in Pharmacology, 2024; 15:1407200.

Yuan et al., "Tetrahydrocurcumin ameliorates diabetes profiles of db/db mice by altering the composition of gut microbiota and up-regulating the expression of GLP-1 in the pancreas," Fitoterapia, 2020; 146:104665.

Zapata et al., "Dietary Tryptophan Restriction Dose-Dependently Modulates Energy Balance, Gut Hormones, and Microbiota in Obesity-Prone Rats," Obesity, 2018; 26(4): pp. 730-739.

Zhao et al., "Nanoparticles prepared from pterostilbene reduce blood glucose and improve diabetes complications," Nanobiotechnology, 2021; 19: 191 (18 pages).

Zheng et al., "Dietary capsaicin and its anti-obesity potency: from mechanism to clinical implications," Bioscience Reports, 2017; 37(3):BSR20170286.

Zheng et al., "Polysaccharides from Chinese herbal medicine for anti-diabetes recent advances," International Journal of Biological Macromolecules, 2019; 121: pp. 1240-1253.

Zhu et al., "Saponins from *Camellia sinensis* Seeds Stimulate GIP Secretion in Mice and STC-1 Cells via SGLT1 and TGR5," Nutrients, 2022; 14(16):3413.

* cited by examiner

GLP-1R AGONIST AND DPP-4 INHIBITOR COMPOSITIONS AND METHODS OF USING

CROSS-REFERENCE TO RELATED APPLICATIONS

This application claims the benefit of U.S. Provisional Application 63/463,191, filed May 1, 2023. The entire contents of this application are incorporated herein by reference in its entirety.

BACKGROUND

As of 2020, the obesity rate of the United States was 41.9%, with a severe obesity rate of 9.2%. Obesity is linked with a higher prevalence of other conditions, such as heart disease, stroke, type 2 diabetes and certain types of cancer, which are among the leading causes of preventable, premature death. Further, obesity severely strains the healthcare system; for example, in 2019, the estimated medical cost of obesity in the United States was nearly $173 billion dollars. Accordingly, researchers have sought to develop compounds to combat the obesity epidemic.

The glucagon-like peptide-1 receptor (GLP-1R) is found on the beta cells on the islets of Langerhans in the pancreas. Activation of the GLP-1R by agonists, such as endogenous glucagon-like peptide-1 (GLP-1), endogenous glucagon, or exogenous incretin mimetics, stimulates a decrease in blood glucose levels following a meal by augmenting the secretion of insulin from beta cells of the islets of Langerhans and inhibiting the release of glucagon from alpha cells of the islets of Langerhans. Consequently, GLP-1R agonists have been widely used to treat diabetes mellitus type 2, and recently, as compounds to promote weight loss. To this end, researchers have developed several GLP-1R agonists that demonstrate insulinotropic activity including, but not limited to dulaglutide (Trulicity®), exenatide (Byetta™, Bydureon BCise®), liraglutide (Victoza®), semaglutide (Ozempic®, Wegovy®, and Rybelsus®), and tirzepatide (Mounjaro™).

The dipeptidyl peptidase-4 (DPP-4) enzyme plays a major role in glucose metabolism, as DPP-4 degrades GLP-1 and, in some cases, exogenous incretin mimetics. Accordingly, researchers have considered DPP-4 inhibitors as alternatives to GLP-1R agonists to achieve similar effects, i.e., treatment of type 2 diabetes and weight loss. To this end, researchers have developed several DPP-4 inhibitors including, but not limited to sitagliptin (Januvia®), vildagliptin (Galvus®), saxagliptin (Onglyza®), linagliptin (Tradjenta®), gemigliptin (Zemiglo®), anagliptin (Suiny®), teneligliptin (Tenelia®), alogliptin (Vipidia®), trelagliptin (Zafatek®), and omarigliptin (Marizev®).

SUMMARY

Given that GLP-1R agonists and DPP-4 inhibitors elicit similar effects, researchers have contemplated using combinations of GLP-1R agonists and DPP-4 inhibitors to further improve the clinical outcome of each single type of compound. Conventional attempts, however, have fallen significantly short, as conventional combination treatments provide only a modest improvement in glycemic control with minimal weight loss benefits, with a combined efficacy comparable to the effects seen for monotherapy with either agent, i.e., an antagonist action. Additionally, conventional combinations have demonstrated significant side effects, including nausea, vomiting, abdominal pain, increased risks of cancer, and acute pancreatitis, among others. Lastly, because the current GLP-1R agonists and DPP-4 inhibitors in conventional combinations comprise small molecule-, peptide-, and protein-based compounds the cost to manufacture and provide these products to patients is exceedingly high.

The inventors sought to develop compositions comprising at least one GLP-1R agonist and at least one DPP-4 inhibitor to overcome the shortcomings of the conventional combination treatments. Accordingly, the inventors have developed compositions comprising low-cost GLP-1R agonists and DPP-4 inhibitors that provide a superior, and unexpected, synergistic outcome for increasing weight loss and/or boosting satiety, without increasing the incidence of negative side effects, and in some instances, reducing the incidence of negative side effects. This finding is novel. As such, by providing at least one GLP-1R agonist and at least one DPP-4 inhibitor together as pharmaceutical agents and/or dietary supplements, therapeutic and/or nutraceutical benefits can be realized, either individually collectively, or in conjunction with other pharmaceutical agents and/or dietary supplements.

Embodiments of the present disclosure relate to novel GLP-1R agonist compositions, novel DPP-4 inhibitor compositions, or compositions comprising the combination thereof and their use to promote weight loss, boost satiety, and/or increase GLP-1 levels.

These and other features, aspects, and advantages of the present embodiments will become understood with reference to the following description and appended claims.

DETAILED DESCRIPTION

Some embodiments provide a composition comprising an amount of one or more GLP-1R agonists formulated as a GLP-1R agonist composition. In certain embodiments, a GLP-1R agonist composition can comprise an amount of a ginseng composition, an amount of a curcumin composition, an amount of a pharmaceutical GLP composition, an amount of a conjugated linoleic acid composition, an amount of a bayberry powder composition, an amount of a berberine composition, an amount of a berberine hydrochloride composition, an amount of a camellia sinensis (matcha) composition, an amount of a capsaicin (chili pepper) composition, an amount of a dong quai root powder composition, an amount of an epigallocatechin gallate (EGCG) composition, an amount of a freeze dried milk (Kefir Powder) composition, an amount of a garcinia cambogia extract (hydroxycitric acid) composition, an amount of a lion's mane mushroom composition, an amount of a medium chain triglycerides composition, an amount of a pterostilbene composition, an amount of a quercetin pure composition, an amount of a resveratrol composition, an amount of a sucralose composition, an amount of a uva ursi leaf composition, or any combination thereof. In some embodiments, a GLP-1R agonist composition, as disclosed herein, may comprise a pharmaceutically acceptable vehicle, carrier, or diluent. Some embodiments can be formulated to have varying amounts of these constituents.

As used herein, a "ginseng composition" defines a composition comprising ginseng root powder and/or an extract of ginseng root. For purposes of this disclosure, an "extract of ginseng root," as used herein, may include, but is not limited to one or more compounds selected from the group the consisting of dammarane, falcarinol, ginsenoside compound K (C-K), ginsenoside Rb0, ginsenoside Rb1, ginsenoside Rb2, ginsenoside Rc, ginsenoside Rd, ginsenoside Re, ginsenoside Rf, ginsenoside Rg1, ginsenoside Rg2, ginsenoside Rg3, ginsenoside Rh1, ginsenoside Rh2, ginsenoside Rh3, oleanane, panaxydol, panaxytriol, protopanaxadiol, protopanaxatriol, and any combination of the foregoing. As used herein, the term "extract of ginseng root" can define a single compound or a mixture of compounds from the foregoing, the usage of these terms will be clear to the skilled artisan in view of their usage in context and in the claims.

When provided in a GLP-1R agonist composition, the amount of a ginseng composition provided may be about 10 μg to about 10 g. For example, the amount of a ginseng composition in the GLP-1R agonist composition can be about 10 μg, 15 μg, 20 μg, 25 μg, 30 μg, 35 μg, 40 μg, 45 μg, 50 μg, 55 μg, 60 μg, 65 μg, 70 μg, 75 μg, 80 μg, 85 μg, 90 μg, 95 μg, 100 μg, 125 μg, 150 μg, 175 μg, 200 μg, 225 μg, 250 μg, 275 μg, 300 μg, 325 μg, 350 μg, 375 μg, 400 μg, 425 μg, 450 μg, 475 μg, 500 μg, 525 μg, 550 μg, 575 μg, 600 μg, 625 μg, 650 μg, 675 μg, 700 μg, 725 μg, 750 μg, 775 μg, 800 μg, 825 μg, 850 μg, 875 μg, 900 μg, 925 μg, 950 μg, 975 μg, 1000 μg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 125 mg, 150 mg, 175 mg, 200 mg, 225 mg, 250 mg, 275 mg, 300 mg, 325 mg, 350 mg, 375 mg, 400 mg, 425 mg, 450 mg, 475 mg, 500 mg, 525 mg, 550 mg, 575 mg, 600 mg, 625 mg, 650 mg, 675 mg, 700 mg, 725 mg, 750 mg, 775 mg, 800 mg, 825 mg, 850 mg, 875 mg, 900 mg, 925 mg, 950 mg, 975 mg, 1.0 g, 1.25 g, 1.50 g, 1.75 g, 2.0 g, 2.25 g, 2.50 g, 2.75 g, 3.0 g, 3.25 g, 3.50 g, 3.75 g, 4.0 g, 4.25 g, 4.50 g, 4.75 g, 5.0 g, 5.25 g, 5.50 g, 5.75 g, 6.0 g, 6.25 g, 6.50 g, 6.75 g, 7.0 g, 7.25 g, 7.50 g, 7.75 g, 8.0 g, 8.25 g, 8.50 g, 8.75 g, 9.0 g, 9.25 g, 9.50 g, 9.75 g, 10.0 g, or any range or amount in between any two of the preceding values and any other ranges or amounts disclosed herein.

As used herein, a "curcumin composition" defines a composition comprising one or more of diferuloylmethane, demethoxycurcumin, bis-demethoxycurcumin, tetrahydrocurcumin, dihydrocurcumin, hexahydrocurcumin, and octahydrocurcumin.

When provided in a GLP-1R agonist composition, the amount of a curcumin composition provided may be about 10 μg to about 10 g. For example, the amount of a curcumin composition in the GLP-1R agonist composition can be about 10 μg, 15 μg, 20 μg, 25 μg, 30 μg, 35 μg, 40 μg, 45 μg, 50 μg, 55 μg, 60 μg, 65 μg, 70 μg, 75 μg, 80 μg, 85 μg, 90 μg, 95 μg, 100 μg, 125 μg, 150 μg, 175 μg, 200 μg, 225 μg, 250 μg, 275 μg, 300 μg, 325 μg, 350 μg, 375 μg, 400 μg, 425 μg, 450 μg, 475 μg, 500 μg, 525 μg, 550 μg, 575 μg, 600 μg, 625 μg, 650 μg, 675 μg, 700 μg, 725 μg, 750 μg, 775 μg, 800 μg, 825 μg, 850 μg, 875 μg, 900 μg, 925 μg, 950 μg, 975 μg, 1000 μg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 125 mg, 150 mg, 175 mg, 200 mg, 225 mg, 250 mg, 275 mg, 300 mg, 325 mg, 350 mg, 375 mg, 400 mg, 425 mg, 450 mg, 475 mg, 500 mg, 525 mg, 550 mg, 575 mg, 600 mg, 625 mg, 650 mg, 675 mg, 700 mg, 725 mg, 750 mg, 775 mg, 800 mg, 825 mg, 850 mg, 875 mg, 900 mg, 925 mg, 950 mg, 975 mg, 1.0 g, 1.25 g, 1.50 g, 1.75 g, 2.0 g, 2.25 g, 2.50 g, 2.75 g, 3.0 g, 3.25 g, 3.50 g, 3.75 g, 4.0 g, 4.25 g, 4.50 g, 4.75 g, 5.0 g, 5.25 g, 5.50 g, 5.75 g, 6.0 g, 6.25 g, 6.50 g, 6.75 g, 7.0 g, 7.25 g, 7.50 g, 7.75 g, 8.0 g, 8.25 g, 8.50 g, 8.75 g, 9.0 g, 9.25 g, 9.50 g, 9.75 g, 10.0 g, or any range or amount in between any two of the preceding values and any other ranges or amounts disclosed herein.

As used herein, a "pharmaceutical GLP composition" defines a composition comprising one or more of GLP-1 analogues, such as dulaglutide, albiglutide, exenatide, liraglutide, semaglutide, lixisenatide, and tirzepatide.

When provided in a GLP-1R agonist composition, the amount of a pharmaceutical GLP composition provided may be about 10 μg to about 30 mg. For example, the amount of a pharmaceutical GLP composition in the GLP-1R agonist composition can be about 10 μg, 15 μg, 20 μg, 25 μg, 30 μg, 35 μg, 40 μg, 45 μg, 50 μg, 55 μg, 60 μg, 65 μg, 70 μg, 75 μg, 80 μg, 85 μg, 90 μg, 95 μg, 100 μg, 125 μg, 150 μg, 175 μg, 200 μg, 225 μg, 250 μg, 275 μg, 300 μg, 325 μg, 350 μg, 375 μg, 400 μg, 425 μg, 450 μg, 475 μg, 500 μg, 525 μg, 550 μg, 575 μg, 600 μg, 625 μg, 650 μg, 675 μg, 700 μg, 725 μg, 750 μg, 775 μg, 800 μg, 825 μg, 850 μg, 875 μg, 900 μg, 925 μg, 950 μg, 975 μg, 1000 μg, 1.5 mg, 2 mg, 2.5 mg, 3 mg, 3.5 mg, 4 mg, 4.5 mg, 5 mg, 5.5 mg, 6 mg, 6.5 mg, 7 mg, 7.5 mg, 8 mg, 8.5 mg, 9 mg, 9.5 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 26 mg, 27 mg, 28 mg, 29 mg, 30 mg, or any range or amount in between any two of the preceding values and any other ranges or amounts disclosed herein.

As used herein, a "conjugated linoleic acid composition" refers to a composition comprising linoleic acid (i.e., a polyunsaturated, omega-6 fatty acid having the chemical name of 18:2ω6; cis, cis-9,12-octadecadienoic acid). When provided in a GLP-1R agonist composition, the amount of a conjugated linoleic acid composition provided may be about 10 μg to about 10 g. For example, the amount of a conjugated linoleic acid composition in the GLP-1R agonist composition can be about 10 μg, 15 μg, 20 μg, 25 μg, 30 μg, 35 μg, 40 μg, 45 μg, 50 μg, 55 μg, 60 μg, 65 μg, 70 μg, 75 μg, 80 μg, 85 μg, 90 μg, 95 μg, 100 μg, 125 μg, 150 μg, 175 μg, 200 μg, 225 μg, 250 μg, 275 μg, 300 μg, 325 μg, 350 μg, 375 μg, 400 μg, 425 μg, 450 μg, 475 μg, 500 μg, 525 μg, 550 μg, 575 μg, 600 μg, 625 μg, 650 μg, 675 μg, 700 μg, 725 μg, 750 μg, 775 μg, 800 μg, 825 μg, 850 μg, 875 μg, 900 μg, 925 μg, 950 μg, 975 μg, 1000 μg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 125 mg, 150 mg, 175 mg, 200 mg, 225 mg, 250 mg, 275 mg, 300 mg, 325 mg, 350 mg, 375 mg, 400 mg, 425 mg, 450 mg, 475 mg, 500 mg, 525 mg, 550 mg, 575 mg, 600 mg, 625 mg, 650 mg, 675 mg, 700 mg, 725 mg, 750 mg, 775 mg, 800 mg, 825 mg, 850 mg, 875 mg, 900 mg, 925 mg, 950 mg, 975 mg, 1.0 g, 1.25 g, 1.50 g, 1.75 g, 2.0 g, 2.25 g, 2.50 g, 2.75 g, 3.0 g, 3.25 g, 3.50 g, 3.75 g, 4.0 g, 4.25 g, 4.50 g, 4.75 g, 5.0 g, 5.25 g, 5.50 g, 5.75 g, 6.0 g, 6.25 g, 6.50 g, 6.75 g, 7.0 g, 7.25 g, 7.50 g, 7.75 g, 8.0 g, 8.25 g, 8.50 g, 8.75 g, 9.0 g, 9.25 g, 9.50 g, 9.75 g, 10.0 g, or any range or amount in between any two of the preceding values and any other ranges or amounts disclosed herein.

As used herein, a "bayberry powder composition" refers to a composition comprising a powdered bayberry extract, a bayberry root bark powder, a bayberry bark powder, a bayberry fruit powder, a bayberry root powder, or any combination thereof. The powdered bayberry extract can be extracts from bayberry root barks, bayberry barks, bayberry fruits, or a combination thereof that are dried and powdered. The bayberry root bark powder, bayberry bark powder, bayberry fruit powder, and bayberry root powder can be derived from drying and powdering root barks, barks, fruits and roots without extraction. When provided in a GLP-1R agonist composition, the amount of a bayberry powder composition provided may be about 10 μg to about 10 g. For example, the amount of a bayberry powder composition in the GLP-1R agonist composition can be about 10 μg, 15 μg, 20 μg, 25 μg, 30 μg, 35 μg, 40 μg, 45 μg, 50 μg, 55 μg, 60 μg, 65 μg, 70 μg, 75 μg, 80 μg, 85 μg, 90 μg, 95 μg, 100 μg, 125 μg, 150 μg, 175 μg, 200 μg, 225 μg, 250 μg, 275 μg, 300 μg, 325 μg, 350 μg, 375 μg, 400 μg, 425 μg, 450 μg, 475 μg, 500 μg, 525 μg, 550 μg, 575 μg, 600 μg, 625 μg, 650 μg, 675 μg, 700 μg, 725 μg, 750 μg, 775 μg, 800 μg, 825 μg, 850 μg, 875 μg, 900 μg, 925 μg, 950 μg, 975 μg, 1000 μg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 125 mg, 150 mg, 175 mg, 200 mg, 225 mg, 250 mg, 275 mg, 300 mg, 325 mg, 350 mg, 375 mg, 400 mg, 425 mg, 450 mg, 475 mg, 500 mg, 525 mg, 550 mg, 575 mg, 600 mg, 625 mg, 650 mg, 675 mg, 700 mg, 725 mg, 750 mg, 775 mg, 800 mg, 825 mg, 850 mg, 875 mg, 900 mg, 925 mg, 950 mg, 975 mg, 1.0 g, 1.25 g, 1.50 g, 1.75 g, 2.0 g, 2.25 g, 2.50 g, 2.75 g, 3.0 g, 3.25 g, 3.50 g, 3.75 g, 4.0 g, 4.25 g, 4.50 g, 4.75 g, 5.0 g, 5.25 g, 5.50 g, 5.75 g, 6.0 g, 6.25 g, 6.50 g, 6.75 g, 7.0 g, 7.25 g, 7.50 g, 7.75 g, 8.0 g, 8.25 g, 8.50 g, 8.75 g, 9.0 g, 9.25 g, 9.50 g, 9.75 g, 10.0 g, or any range or amount in between any two of the preceding values and any other ranges or amounts disclosed herein.

As used herein, a "berberine composition" refers to a composition comprising compound berberine (an isoquinoline alkaloid) and a "berberine hydrochloride composition" refers to a composition comprising a hydrochloride salt form of berberine. When provided in a GLP-1R agonist composition, the amount of a berberine composition, the amount of a berberine hydrochloride composition, or a combination thereof provided may be about 10 μg to about 10 g. For example, the amount of a berberine composition, a berberine hydrochloride composition, or a combination thereof in the GLP-1R agonist composition can be about 10 μg, 15 μg, 20 μg, 25 μg, 30 μg, 35 μg, 40 μg, 45 μg, 50 μg, 55 μg, 60 μg, 65 μg, 70 μg, 75 μg, 80 μg, 85 μg, 90 μg, 95 μg, 100 μg, 125 μg, 150 μg, 175 μg, 200 μg, 225 μg, 250 μg, 275 μg, 300 μg, 325 μg, 350 μg, 375 μg, 400 μg, 425 μg, 450 μg, 475 μg, 500 μg, 525 μg, 550 μg, 575 μg, 600 μg, 625 μg, 650 μg, 675 μg, 700 μg, 725 μg, 750 μg, 775 μg, 800 μg, 825 μg, 850 μg, 875 μg, 900 μg, 925 μg, 950 μg, 975 μg, 1000 μg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 125 mg, 150 mg, 175 mg, 200 mg, 225 mg, 250 mg, 275 mg, 300 mg, 325 mg, 350 mg, 375 mg, 400 mg, 425 mg, 450 mg, 475 mg, 500 mg, 525 mg, 550 mg, 575 mg, 600 mg, 625 mg, 650 mg, 675 mg, 700 mg, 725 mg, 750 mg, 775 mg, 800 mg, 825 mg, 850 mg, 875 mg, 900 mg, 925 mg, 950 mg, 975 mg, 1.0 g, 1.25 g, 1.50 g, 1.75 g, 2.0 g, 2.25 g, 2.50 g, 2.75 g, 3.0 g, 3.25 g, 3.50 g, 3.75 g, 4.0 g, 4.25 g, 4.50 g, 4.75 g, 5.0 g, 5.25 g, 5.50 g, 5.75 g, 6.0 g, 6.25 g, 6.50 g, 6.75 g, 7.0 g, 7.25 g, 7.50 g, 7.75 g, 8.0 g, 8.25 g, 8.50 g, 8.75 g, 9.0 g, 9.25 g, 9.50 g, 9.75 g, 10.0 g, or any range or amount in between any two of the preceding values and any other ranges or amounts disclosed herein.

As used herein, a "camellia sinensis (matcha) composition" refers to a composition comprising powdered camellia sinensis leaves, powdered camellia sinensis leaf buds, powdered camellia sinensis stems, powdered camellia sinensis leaf extract or a combination thereof. When provided in a GLP-1R agonist composition, the amount of a camellia sinensis (matcha) composition provided may be about 10 μg to about 10 g. For example, the amount of a camellia sinensis (matcha) composition in the GLP-1R agonist composition can be about 10 μg, 15 μg, 20 μg, 25 μg, 30 μg, 35 μg, 40 μg, 45 μg, 50 μg, 55 μg, 60 μg, 65 μg, 70 μg, 75 μg, 80 μg, 85 μg, 90 μg, 95 μg, 100 μg, 125 μg, 150 μg, 175 μg, 200 μg, 225 μg, 250 μg, 275 μg, 300 μg, 325 μg, 350 μg, 375

μg, 400 μg, 425 μg, 450 μg, 475 μg, 500 μg, 525 μg, 550 μg, 575 μg, 600 μg, 625 μg, 650 μg, 675 μg, 700 μg, 725 μg, 750 μg, 775 μg, 800 μg, 825 μg, 850 μg, 875 μg, 900 μg, 925 μg, 950 μg, 975 μg, 1000 μg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 125 mg, 150 mg, 175 mg, 200 mg, 225 mg, 250 mg, 275 mg, 300 mg, 325 mg, 350 mg, 375 mg, 400 mg, 425 mg, 450 mg, 475 mg, 500 mg, 525 mg, 550 mg, 575 mg, 600 mg, 625 mg, 650 mg, 675 mg, 700 mg, 725 mg, 750 mg, 775 mg, 800 mg, 825 mg, 850 mg, 875 mg, 900 mg, 925 mg, 950 mg, 975 mg, 1.0 g, 1.25 g, 1.50 g, 1.75 g, 2.0 g, 2.25 g, 2.50 g, 2.75 g, 3.0 g, 3.25 g, 3.50 g, 3.75 g, 4.0 g, 4.25 g, 4.50 g, 4.75 g, 5.0 g, 5.25 g, 5.50 g, 5.75 g, 6.0 g, 6.25 g, 6.50 g, 6.75 g, 7.0 g, 7.25 g, 7.50 g, 7.75 g, 8.0 g, 8.25 g, 8.50 g, 8.75 g, 9.0 g, 9.25 g, 9.50 g, 9.75 g, 10.0 g, or any range or amount in between any two of the preceding values and any other ranges or amounts disclosed herein.

As used herein, a "capsaicin (chili pepper) composition" refers to a composition comprising compound capsaicin having the chemical name of 8-methyl-N-vanillyl-6-nonenamide, which is an active ingredient of chili pepper. When provided in a GLP-1R agonist composition, the amount of a capsaicin (chili pepper) composition provided may be about 10 μg to about 10 g. For example, the amount of a capsaicin (chili pepper) composition in the GLP-1R agonist composition can be about 10 μg, 15 μg, 20 μg, 25 μg, 30 μg, 35 μg, 40 μg, 45 μg, 50 μg, 55 μg, 60 μg, 65 μg, 70 μg, 75 μg, 80 μg, 85 μg, 90 μg, 95 μg, 100 μg, 125 μg, 150 μg, 175 μg, 200 μg, 225 μg, 250 μg, 275 μg, 300 μg, 325 μg, 350 μg, 375 μg, 400 μg, 425 μg, 450 μg, 475 μg, 500 μg, 525 μg, 550 μg, 575 μg, 600 μg, 625 μg, 650 μg, 675 μg, 700 μg, 725 μg, 750 μg, 775 μg, 800 μg, 825 μg, 850 μg, 875 μg, 900 μg, 925 μg, 950 μg, 975 μg, 1000 μg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 125 mg, 150 mg, 175 mg, 200 mg, 225 mg, 250 mg, 275 mg, 300 mg, 325 mg, 350 mg, 375 mg, 400 mg, 425 mg, 450 mg, 475 mg, 500 mg, 525 mg, 550 mg, 575 mg, 600 mg, 625 mg, 650 mg, 675 mg, 700 mg, 725 mg, 750 mg, 775 mg, 800 mg, 825 mg, 850 mg, 875 mg, 900 mg, 925 mg, 950 mg, 975 mg, 1.0 g, 1.25 g, 1.50 g, 1.75 g, 2.0 g, 2.25 g, 2.50 g, 2.75 g, 3.0 g, 3.25 g, 3.50 g, 3.75 g, 4.0 g, 4.25 g, 4.50 g, 4.75 g, 5.0 g, 5.25 g, 5.50 g, 5.75 g, 6.0 g, 6.25 g, 6.50 g, 6.75 g, 7.0 g, 7.25 g, 7.50 g, 7.75 g, 8.0 g, 8.25 g, 8.50 g, 8.75 g, 9.0 g, 9.25 g, 9.50 g, 9.75 g, 10.0 g, or any range or amount in between any two of the preceding values and any other ranges or amounts disclosed herein.

As used herein, a "dong quai root powder composition" refers to a composition comprising a powdered dong quai root extract, a dong quai root powder, or a combination thereof. A powdered dong quai root extract can be obtained by extracting dong quai roots using standard extraction technology in the field and the resultant extract was dried and powdered. A dong quai root powder can be obtained by (i) drying the roots and then pulverizing the dried roots or (ii) by pulverizing fresh roots followed by drying. When provided in a GLP-1R agonist composition, the amount of a dong quai root powder composition provided may be about 10 μg to about 10 g. For example, the amount of a dong quai root powder composition in the GLP-1R agonist composition can be about 10 μg, 15 μg, 20 μg, 25 μg, 30 μg, 35 μg, 40 μg, 45 μg, 50 μg, 55 μg, 60 μg, 65 μg, 70 μg, 75 μg, 80 μg, 85 μg, 90 μg, 95 μg, 100 μg, 125 μg, 150 μg, 175 μg, 200 μg, 225 μg, 250 μg, 275 μg, 300 μg, 325 μg, 350 μg, 375 μg, 400 μg, 425 μg, 450 μg, 475 μg, 500 μg, 525 μg, 550 μg, 575 μg, 600 μg, 625 μg, 650 μg, 675 μg, 700 μg, 725 μg, 750 μg, 775 µg, 800 µg, 825 µg, 850 µg, 875 µg, 900 µg, 925 µg, 950 µg, 975 µg, 1000 µg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 125 mg, 150 mg, 175 mg, 200 mg, 225 mg, 250 mg, 275 mg, 300 mg, 325 mg, 350 mg, 375 mg, 400 mg, 425 mg, 450 mg, 475 mg, 500 mg, 525 mg, 550 mg, 575 mg, 600 mg, 625 mg, 650 mg, 675 mg, 700 mg, 725 mg, 750 mg, 775 mg, 800 mg, 825 mg, 850 mg, 875 mg, 900 mg, 925 mg, 950 mg, 975 mg, 1.0 g, 1.25 g, 1.50 g, 1.75 g, 2.0 g, 2.25 g, 2.50 g, 2.75 g, 3.0 g, 3.25 g, 3.50 g, 3.75 g, 4.0 g, 4.25 g, 4.50 g, 4.75 g, 5.0 g, 5.25 g, 5.50 g, 5.75 g, 6.0 g, 6.25 g, 6.50 g, 6.75 g, 7.0 g, 7.25 g, 7.50 g, 7.75 g, 8.0 g, 8.25 g, 8.50 g, 8.75 g, 9.0 g, 9.25 g, 9.50 g, 9.75 g, 10.0 g, or any range or amount in between any two of the preceding values and any other ranges or amounts disclosed herein.

As used herein, an "epigallocatechin gallate (EGCG) composition" refers to a composition comprising EGCG (i.e., the ester of epigallocatechin and gallic acid and a type of catechin). When provided in a GLP-1R agonist composition, the amount of an EGCG composition provided may be about 10 µg to about 10 g. For example, the amount of an EGCG composition in the GLP-1R agonist composition can be about 10 µg, 15 µg, 20 µg, 25 µg, 30 µg, 35 µg, 40 µg, 45 µg, 50 µg, 55 µg, 60 µg, 65 µg, 70 µg, 75 µg, 80 µg, 85 µg, 90 µg, 95 µg, 100 µg, 125 µg, 150 µg, 175 µg, 200 µg, 225 µg, 250 µg, 275 µg, 300 µg, 325 µg, 350 µg, 375 µg, 400 µg, 425 µg, 450 µg, 475 µg, 500 µg, 525 µg, 550 µg, 575 µg, 600 µg, 625 µg, 650 µg, 675 µg, 700 µg, 725 µg, 750 µg, 775 µg, 800 µg, 825 µg, 850 µg, 875 µg, 900 µg, 925 µg, 950 µg, 975 µg, 1000 µg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 125 mg, 150 mg, 175 mg, 200 mg, 225 mg, 250 mg, 275 mg, 300 mg, 325 mg, 350 mg, 375 mg, 400 mg, 425 mg, 450 mg, 475 mg, 500 mg, 525 mg, 550 mg, 575 mg, 600 mg, 625 mg, 650 mg, 675 mg, 700 mg, 725 mg, 750 mg, 775 mg, 800 mg, 825 mg, 850 mg, 875 mg, 900 mg, 925 mg, 950 mg, 975 mg, 1.0 g, 1.25 g, 1.50 g, 1.75 g, 2.0 g, 2.25 g, 2.50 g, 2.75 g, 3.0 g, 3.25 g, 3.50 g, 3.75 g, 4.0 g, 4.25 g, 4.50 g, 4.75 g, 5.0 g, 5.25 g, 5.50 g, 5.75 g, 6.0 g, 6.25 g, 6.50 g, 6.75 g, 7.0 g, 7.25 g, 7.50 g, 7.75 g, 8.0 g, 8.25 g, 8.50 g, 8.75 g, 9.0 g, 9.25 g, 9.50 g, 9.75 g, 10.0 g, or any range or amount in between any two of the preceding values and any other ranges or amounts disclosed herein.

As used herein, a "freeze dried milk (Kefir Powder) composition" refers to a composition comprising Kefir Powder. When provided in a GLP-1R agonist composition, the amount of a Kefir Powder composition provided may be about 10 µg to about 10 g. For example, the amount of a Kefir Powder composition in the GLP-1R agonist composition can be about 10 µg, 15 µg, 20 µg, 25 µg, 30 µg, 35 µg, 40 µg, 45 µg, 50 µg, 55 µg, 60 µg, 65 µg, 70 µg, 75 µg, 80 µg, 85 µg, 90 µg, 95 µg, 100 µg, 125 µg, 150 µg, 175 µg, 200 µg, 225 µg, 250 µg, 275 µg, 300 µg, 325 µg, 350 µg, 375 µg, 400 µg, 425 µg, 450 µg, 475 µg, 500 µg, 525 µg, 550 µg, 575 µg, 600 µg, 625 µg, 650 µg, 675 µg, 700 µg, 725 µg, 750 µg, 775 µg, 800 µg, 825 µg, 850 µg, 875 µg, 900 µg, 925 µg, 950 µg, 975 µg, 1000 µg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 125 mg, 150 mg, 175 mg, 200 mg, 225 mg, 250 mg, 275 mg, 300 mg, 325 mg, 350 mg, 375 mg, 400 mg, 425 mg, 450 mg, 475 mg, 500 mg, 525 mg, 550 mg, 575 mg, 600 mg, 625 mg, 650 mg, 675 mg, 700 mg, 725 mg, 750 mg, 775 mg, 800 mg, 825 mg, 850 mg, 875 mg, 900 mg, 925 mg, 950 mg, 975 mg, 1.0 g, 1.25 g, 1.50 g, 1.75 g, 2.0 g, 2.25 g, 2.50 g, 2.75 g, 3.0 g, 3.25 g, 3.50 g, 3.75 g, 4.0 g, 4.25 g, 4.50 g, 4.75 g, 5.0 g, 5.25 g, 5.50 g, 5.75 g, 6.0 g, 6.25 g, 6.50 g, 6.75 g, 7.0 g, 7.25 g, 7.50 g, 7.75 g, 8.0 g, 8.25 g, 8.50 g, 8.75 g, 9.0 g, 9.25 g, 9.50 g, 9.75 g, 10.0 g, or any range or amount in between any two of the preceding values and any other ranges or amounts disclosed herein.

As used herein, a "garcinia cambogia extract (hydroxycitric acid) composition" refers to a composition comprising garcinia cambogia extract with hydroxycitric acid as an active ingredient. When provided in a GLP-1R agonist composition, the amount of a garcinia cambogia extract composition provided may be about 10 µg to about 10 g. For example, the amount of a garcinia cambogia extract composition in the GLP-1R agonist composition can be about 10 µg, 15 µg, 20 µg, 25 µg, 30 µg, 35 µg, 40 µg, 45 µg, 50 µg, 55 µg, 60 µg, 65 µg, 70 µg, 75 µg, 80 µg, 85 µg, 90 µg, 95 µg, 100 µg, 125 µg, 150 µg, 175 µg, 200 µg, 225 µg, 250 µg, 275 µg, 300 µg, 325 µg, 350 µg, 375 µg, 400 µg, 425 µg, 450 µg, 475 µg, 500 µg, 525 µg, 550 µg, 575 µg, 600 µg, 625 µg, 650 µg, 675 µg, 700 µg, 725 µg, 750 µg, 775 µg, 800 µg, 825 µg, 850 µg, 875 µg, 900 µg, 925 µg, 950 µg, 975 µg, 1000 µg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 125 mg, 150 mg, 175 mg, 200 mg, 225 mg, 250 mg, 275 mg, 300 mg, 325 mg, 350 mg, 375 mg, 400 mg, 425 mg, 450 mg, 475 mg, 500 mg, 525 mg, 550 mg, 575 mg, 600 mg, 625 mg, 650 mg, 675 mg, 700 mg, 725 mg, 750 mg, 775 mg, 800 mg, 825 mg, 850 mg, 875 mg, 900 mg, 925 mg, 950 mg, 975 mg, 1.0 g, 1.25 g, 1.50 g, 1.75 g, 2.0 g, 2.25 g, 2.50 g, 2.75 g, 3.0 g, 3.25 g, 3.50 g, 3.75 g, 4.0 g, 4.25 g, 4.50 g, 4.75 g, 5.0 g, 5.25 g, 5.50 g, 5.75 g, 6.0 g, 6.25 g, 6.50 g, 6.75 g, 7.0 g, 7.25 g, 7.50 g, 7.75 g, 8.0 g, 8.25 g, 8.50 g, 8.75 g, 9.0 g, 9.25 g, 9.50 g, 9.75 g, 10.0 g, or any range or amount in between any two of the preceding values and any other ranges or amounts disclosed herein.

As used herein, a "lion's mane mushroom composition" refers to a composition comprising a lion's mane mushroom powder, which can be dried and powdered fruiting body of the lion's mane mushroom, the dried and powdered extract of lion's mane mushroom, or a combination thereof. When provided in a GLP-1R agonist composition, the amount of a lion's mane mushroom composition provided may be about 10 µg to about 10 g. For example, the amount of a lion's mane mushroom composition in the GLP-1R agonist composition can be about 10 µg, 15 µg, 20 µg, 25 µg, 30 µg, 35 µg, 40 µg, 45 µg, 50 µg, 55 µg, 60 µg, 65 µg, 70 µg, 75 µg, 80 µg, 85 µg, 90 µg, 95 µg, 100 µg, 125 µg, 150 µg, 175 µg, 200 µg, 225 µg, 250 µg, 275 µg, 300 µg, 325 µg, 350 µg, 375 µg, 400 µg, 425 µg, 450 µg, 475 µg, 500 µg, 525 µg, 550 µg, 575 µg, 600 µg, 625 µg, 650 µg, 675 µg, 700 µg, 725 µg, 750 µg, 775 µg, 800 µg, 825 µg, 850 µg, 875 µg, 900 µg, 925 µg, 950 µg, 975 µg, 1000 µg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 125 mg, 150 mg, 175 mg, 200 mg, 225 mg, 250 mg, 275 mg, 300 mg, 325 mg, 350 mg, 375 mg, 400 mg, 425 mg, 450 mg, 475 mg, 500 mg, 525 mg, 550 mg, 575 mg, 600 mg, 625 mg, 650 mg, 675 mg, 700 mg, 725 mg, 750 mg, 775 mg, 800 mg, 825 mg, 850 mg, 875 mg, 900 mg, 925 mg, 950 mg, 975 mg, 1.0 g, 1.25 g, 1.50 g, 1.75 g, 2.0 g, 2.25 g, 2.50 g, 2.75 g, 3.0 g, 3.25 g, 3.50 g, 3.75 g, 4.0 g, 4.25 g, 4.50 g, 4.75 g, 5.0 g, 5.25 g, 5.50 g, 5.75 g, 6.0 g, 6.25 g, 6.50 g, 6.75 g, 7.0 g, 7.25 g, 7.50 g, 7.75 g, 8.0 g, 8.25 g, 8.50 g, 8.75 g, 9.0 g, 9.25 g, 9.50 g, 9.75 g, 10.0 g, or any range or amount in between any two of the preceding values and any other ranges or amounts disclosed herein.

As used herein, a "medium chain triglycerides composition" refers to a composition comprising fatty acids that have a chain length of 6-12 carbon atoms. When provided in a GLP-1R agonist composition, the amount of a medium chain triglycerides composition provided may be about 10 μg to about 10 g. For example, the amount of a medium chain triglycerides composition in the GLP-1R agonist composition can be about 10 μg, 15 μg, 20 μg, 25 μg, 30 μg, 35 μg, 40 μg, 45 μg, 50 μg, 55 μg, 60 μg, 65 μg, 70 μg, 75 μg, 80 μg, 85 μg, 90 μg, 95 μg, 100 μg, 125 μg, 150 μg, 175 μg, 200 μg, 225 μg, 250 μg, 275 μg, 300 μg, 325 μg, 350 μg, 375 μg, 400 μg, 425 μg, 450 μg, 475 μg, 500 μg, 525 μg, 550 μg, 575 μg, 600 μg, 625 μg, 650 μg, 675 μg, 700 μg, 725 μg, 750 μg, 775 μg, 800 μg, 825 μg, 850 μg, 875 μg, 900 μg, 925 μg, 950 μg, 975 μg, 1000 μg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 125 mg, 150 mg, 175 mg, 200 mg, 225 mg, 250 mg, 275 mg, 300 mg, 325 mg, 350 mg, 375 mg, 400 mg, 425 mg, 450 mg, 475 mg, 500 mg, 525 mg, 550 mg, 575 mg, 600 mg, 625 mg, 650 mg, 675 mg, 700 mg, 725 mg, 750 mg, 775 mg, 800 mg, 825 mg, 850 mg, 875 mg, 900 mg, 925 mg, 950 mg, 975 mg, 1.0 g, 1.25 g, 1.50 g, 1.75 g, 2.0 g, 2.25 g, 2.50 g, 2.75 g, 3.0 g, 3.25 g, 3.50 g, 3.75 g, 4.0 g, 4.25 g, 4.50 g, 4.75 g, 5.0 g, 5.25 g, 5.50 g, 5.75 g, 6.0 g, 6.25 g, 6.50 g, 6.75 g, 7.0 g, 7.25 g, 7.50 g, 7.75 g, 8.0 g, 8.25 g, 8.50 g, 8.75 g, 9.0 g, 9.25 g, 9.50 g, 9.75 g, 10.0 g, or any range or amount in between any two of the preceding values and any other ranges or amounts disclosed herein.

As used herein, a "pterostilbene composition" refers to a composition comprising compound pterostilbene that has a chemical name of 4-(3,5-dimethoxystyryl) phenol. When provided in a GLP-1R agonist composition, the amount of a pterostilbene composition provided may be about 10 μg to about 10 g. For example, the amount of a pterostilbene composition in the GLP-1R agonist composition can be about 10 μg, 15 μg, 20 μg, 25 μg, 30 μg, 35 μg, 40 μg, 45 μg, 50 μg, 55 μg, 60 μg, 65 μg, 70 μg, 75 μg, 80 μg, 85 μg, 90 μg, 95 μg, 100 μg, 125 μg, 150 μg, 175 μg, 200 μg, 225 μg, 250 μg, 275 μg, 300 μg, 325 μg, 350 μg, 375 μg, 400 μg, 425 μg, 450 μg, 475 μg, 500 μg, 525 μg, 550 μg, 575 μg, 600 μg, 625 μg, 650 μg, 675 μg, 700 μg, 725 μg, 750 μg, 775 μg, 800 μg, 825 μg, 850 μg, 875 μg, 900 μg, 925 μg, 950 μg, 975 μg, 1000 μg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 125 mg, 150 mg, 175 mg, 200 mg, 225 mg, 250 mg, 275 mg, 300 mg, 325 mg, 350 mg, 375 mg, 400 mg, 425 mg, 450 mg, 475 mg, 500 mg, 525 mg, 550 mg, 575 mg, 600 mg, 625 mg, 650 mg, 675 mg, 700 mg, 725 mg, 750 mg, 775 mg, 800 mg, 825 mg, 850 mg, 875 mg, 900 mg, 925 mg, 950 mg, 975 mg, 1.0 g, 1.25 g, 1.50 g, 1.75 g, 2.0 g, 2.25 g, 2.50 g, 2.75 g, 3.0 g, 3.25 g, 3.50 g, 3.75 g, 4.0 g, 4.25 g, 4.50 g, 4.75 g, 5.0 g, 5.25 g, 5.50 g, 5.75 g, 6.0 g, 6.25 g, 6.50 g, 6.75 g, 7.0 g, 7.25 g, 7.50 g, 7.75 g, 8.0 g, 8.25 g, 8.50 g, 8.75 g, 9.0 g, 9.25 g, 9.50 g, 9.75 g, 10.0 g, or any range or amount in between any two of the preceding values and any other ranges or amounts disclosed herein.

As used herein, a "quercetin pure composition" refers to a composition comprising quercetin (i.e., a flavonoid found in fruits and vegetables) having less than 5% of impurity by weight. When provided in a GLP-1R agonist composition, the amount of a quercetin pure composition provided may be about 10 μg to about 10 g. For example, the amount of a quercetin pure composition in the GLP-1R agonist composition can be about 10 μg, 15 μg, 20 μg, 25 μg, 30 μg, 35 μg, 40 μg, 45 μg, 50 μg, 55 μg, 60 μg, 65 μg, 70 μg, 75 μg, 80 μg, 85 μg, 90 μg, 95 μg, 100 μg, 125 μg, 150 μg, 175 μg, 200 μg, 225 μg, 250 μg, 275 μg, 300 μg, 325 μg, 350 μg, 375 μg, 400 μg, 425 μg, 450 μg, 475 μg, 500 μg, 525 μg, 550 μg, 575 μg, 600 μg, 625 μg, 650 μg, 675 μg, 700 μg, 725 μg, 750 μg, 775 μg, 800 μg, 825 μg, 850 μg, 875 μg, 900 μg, 925 μg, 950 μg, 975 μg, 1000 μg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 125 mg, 150 mg, 175 mg, 200 mg, 225 mg, 250 mg, 275 mg, 300 mg, 325 mg, 350 mg, 375 mg, 400 mg, 425 mg, 450 mg, 475 mg, 500 mg, 525 mg, 550 mg, 575 mg, 600 mg, 625 mg, 650 mg, 675 mg, 700 mg, 725 mg, 750 mg, 775 mg, 800 mg, 825 mg, 850 mg, 875 mg, 900 mg, 925 mg, 950 mg, 975 mg, 1.0 g, 1.25 g, 1.50 g, 1.75 g, 2.0 g, 2.25 g, 2.50 g, 2.75 g, 3.0 g, 3.25 g, 3.50 g, 3.75 g, 4.0 g, 4.25 g, 4.50 g, 4.75 g, 5.0 g, 5.25 g, 5.50 g, 5.75 g, 6.0 g, 6.25 g, 6.50 g, 6.75 g, 7.0 g, 7.25 g, 7.50 g, 7.75 g, 8.0 g, 8.25 g, 8.50 g, 8.75 g, 9.0 g, 9.25 g, 9.50 g, 9.75 g, 10.0 g, or any range or amount in between any two of the preceding values and any other ranges or amounts disclosed herein.

As used herein, a "resveratrol composition" refers to a composition comprising compound resveratrol (i.e., a compound having the chemical name of 3,5,4'-trihydroxystilbene). When provided in a GLP-1R agonist composition, the amount of a resveratrol composition provided may be about 10 μg to about 10 g. For example, the amount of a resveratrol composition in the GLP-1R agonist composition can be about 10 μg, 15 μg, 20 μg, 25 μg, 30 μg, 35 μg, 40 μg, 45 μg, 50 μg, 55 μg, 60 μg, 65 μg, 70 μg, 75 μg, 80 μg, 85 μg, 90 μg, 95 μg, 100 μg, 125 μg, 150 μg, 175 μg, 200 μg, 225 μg, 250 μg, 275 μg, 300 μg, 325 μg, 350 μg, 375 μg, 400 μg, 425 μg, 450 μg, 475 μg, 500 μg, 525 μg, 550 μg, 575 μg, 600 μg, 625 μg, 650 μg, 675 μg, 700 μg, 725 μg, 750 μg, 775 μg, 800 μg, 825 μg, 850 μg, 875 μg, 900 μg, 925 μg, 950 μg, 975 μg, 1000 μg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 125 mg, 150 mg, 175 mg, 200 mg, 225 mg, 250 mg, 275 mg, 300 mg, 325 mg, 350 mg, 375 mg, 400 mg, 425 mg, 450 mg, 475 mg, 500 mg, 525 mg, 550 mg, 575 mg, 600 mg, 625 mg, 650 mg, 675 mg, 700 mg, 725 mg, 750 mg, 775 mg, 800 mg, 825 mg, 850 mg, 875 mg, 900 mg, 925 mg, 950 mg, 975 mg, 1.0 g, 1.25 g, 1.50 g, 1.75 g, 2.0 g, 2.25 g, 2.50 g, 2.75 g, 3.0 g, 3.25 g, 3.50 g, 3.75 g, 4.0 g, 4.25 g, 4.50 g, 4.75 g, 5.0 g, 5.25 g, 5.50 g, 5.75 g, 6.0 g, 6.25 g, 6.50 g, 6.75 g, 7.0 g, 7.25 g, 7.50 g, 7.75 g, 8.0 g, 8.25 g, 8.50 g, 8.75 g, 9.0 g, 9.25 g, 9.50 g, 9.75 g, 10.0 g, or any range or amount in between any two of the preceding values and any other ranges or amounts disclosed herein.

As used herein, a "sucralose composition" refers to a composition comprising sucralose (i.e., an artificial sweetener that stimulates GLP-1 release via sweet taste receptors on enteroendocrine cells). When provided in a GLP-1R agonist composition, the amount of a sucralose composition provided may be about 10 μg to about 30 mg. For example, the amount of a sucralose composition in the GLP-1R agonist composition can be about 10 μg, 15 μg, 20 μg, 25 μg, 30 μg, 35 μg, 40 μg, 45 μg, 50 μg, 55 μg, 60 μg, 65 μg, 70 μg, 75 μg, 80 μg, 85 μg, 90 μg, 95 μg, 100 μg, 125 μg, 150 μg, 175 μg, 200 μg, 225 μg, 250 μg, 275 μg, 300 μg, 325 μg, 350 μg, 375 μg, 400 μg, 425 μg, 450 μg, 475 μg, 500 μg, 525 μg, 550 μg, 575 μg, 600 μg, 625 μg, 650 μg, 675 μg, 700 μg, 725 μg, 750 μg, 775 μg, 800 μg, 825 μg, 850 μg, 875 μg, 900 μg, 925 μg, 950 μg, 975 μg, 1000 μg, 1.5 mg, 2 mg, 2.5 mg, 3 mg, 3.5 mg, 4 mg, 4.5 mg, 5 mg, 5.5 mg, 6 mg, 6.5 mg, 7 mg, 7.5 mg, 8 mg, 8.5 mg, 9 mg, 9.5 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 26 mg, 27 mg, 28 mg, 29 mg, 30 mg, or any range or amount in between any two of the preceding values and any other ranges or amounts disclosed herein.

As used herein, a "uva ursi leaf powder composition" refers to a composition comprising a uva ursi leaf powder, which can be dried and powdered leaf of uva ursi, the dried and powdered extract of uva ursi leaf, or a combination thereof. When provided in a GLP-1R agonist composition, the amount of a uva ursi leaf powder composition provided may be about 10 μg to about 10 g. For example, the amount of a uva ursi leaf powder composition in the GLP-1R agonist composition can be about 10 μg, 15 μg, 20 μg, 25 μg, 30 μg, 35 μg, 40 μg, 45 μg, 50 μg, 55 μg, 60 μg, 65 μg, 70 μg, 75 μg, 80 μg, 85 μg, 90 μg, 95 μg, 100 μg, 125 μg, 150 μg, 175 μg, 200 μg, 225 μg, 250 μg, 275 μg, 300 μg, 325 μg, 350 μg, 375 μg, 400 μg, 425 μg, 450 μg, 475 μg, 500 μg, 525 μg, 550 μg, 575 μg, 600 μg, 625 μg, 650 μg, 675 μg, 700 μg, 725 μg, 750 μg, 775 μg, 800 μg, 825 μg, 850 μg, 875 μg, 900 μg, 925 μg, 950 μg, 975 μg, 1000 μg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 125 mg, 150 mg, 175 mg, 200 mg, 225 mg, 250 mg, 275 mg, 300 mg, 325 mg, 350 mg, 375 mg, 400 mg, 425 mg, 450 mg, 475 mg, 500 mg, 525 mg, 550 mg, 575 mg, 600 mg, 625 mg, 650 mg, 675 mg, 700 mg, 725 mg, 750 mg, 775 mg, 800 mg, 825 mg, 850 mg, 875 mg, 900 mg, 925 mg, 950 mg, 975 mg, 1.0 g, 1.25 g, 1.50 g, 1.75 g, 2.0 g, 2.25 g, 2.50 g, 2.75 g, 3.0 g, 3.25 g, 3.50 g, 3.75 g, 4.0 g, 4.25 g, 4.50 g, 4.75 g, 5.0 g, 5.25 g, 5.50 g, 5.75 g, 6.0 g, 6.25 g, 6.50 g, 6.75 g, 7.0 g, 7.25 g, 7.50 g, 7.75 g, 8.0 g, 8.25 g, 8.50 g, 8.75 g, 9.0 g, 9.25 g, 9.50 g, 9.75 g, 10.0 g, or any range or amount in between any two of the preceding values and any other ranges or amounts disclosed herein.

It is understood that GLP-1R agonists in a GLP-1R agonist composition described herein are not limited to the compositions set forth above and any foods, nutrients, botanicals, and supplements activating GLP-1R can also be included in a GLP-1R agonist composition.

Some embodiments provide a composition comprising an amount of one or more DPP-4 inhibitors formulated as a DPP-4 inhibitor composition. In certain embodiments, a DPP-4 inhibitor composition can comprise an amount of a stilbenoid composition, an amount of a protoberberine composition, an amount of a pharmaceutical DPP composition, an amount of a hydroxycitric acid composition, an amount of an EGCG composition, an amount of a sucralose composition, an amount of a bayberry powder composition, an amount of a camellia sinensis (matcha) powder composition, an amount of a lion's mane mushroom powder composition, an amount of a uva ursi leaf powder composition, an amount of a capsaicin (chili pepper) composition, an amount of a curcumin composition, an amount of a freeze dried milk (Kefir Powder) composition, an amount of a medium chain triglycerides composition, and an amount of a conjugated linoleic acid composition, or any combination thereof. In some embodiments, a DPP-4 inhibitor composition, as described herein, may comprise a pharmaceutically acceptable vehicle, carrier, or diluent. Some embodiments can be formulated to have varying amounts of the foregoing constituents.

As used herein, a "stilbenoid composition" defines a composition comprising one or more of the following compounds: climacostol, desoxyrhapontigenin, dihydropinosylvin monomethyl ether, dihydroresveratrol, gnetol, isorhapontigenin, isoresveratrol, oxyresveratrol, piceatannol, pinostilbene, pinosylvin, pinosylvin monomethyl ether, pterostilbene, resveratrol, rhapontigenin, triacetylresveratrol, trimethylresveratrol, 3'-hydroxypterostilbene, 3,4'-dimethoxy resveratrol, 3,5-dihydroxy-4-ethyl-trans-stilbene, 3,5-dihydroxy-4-isopropylstilbene, 4'-bromo-resveratrol, 4,4'-dihydroxystilbene, or any glycosylated derivate of the foregoing.

When provided in a DPP-4 inhibitor composition, the amount of a stilbenoid composition provided may be about 10 μg to about 10 g. For example, the amount of a stilbenoid composition in the DPP-4 inhibitor composition can be about 10 μg, 15 μg, 20 μg, 25 μg, 30 μg, 35 μg, 40 μg, 45 μg, 50 μg, 55 μg, 60 μg, 65 μg, 70 μg, 75 μg, 80 μg, 85 μg, 90 μg, 95 μg, 100 μg, 125 μg, 150 μg, 175 μg, 200 μg, 225 μg, 250 μg, 275 μg, 300 μg, 325 μg, 350 μg, 375 μg, 400 μg, 425 μg, 450 μg, 475 μg, 500 μg, 525 μg, 550 μg, 575 μg, 600 μg, 625 μg, 650 μg, 675 μg, 700 μg, 725 μg, 750 μg, 775 μg, 800 μg, 825 μg, 850 μg, 875 μg, 900 μg, 925 μg, 950 μg, 975 μg, 1000 μg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 125 mg, 150 mg, 175 mg, 200 mg, 225 mg, 250 mg, 275 mg, 300 mg, 325 mg, 350 mg, 375 mg, 400 mg, 425 mg, 450 mg, 475 mg, 500 mg, 525 mg, 550 mg, 575 mg, 600 mg, 625 mg, 650 mg, 675 mg, 700 mg, 725 mg, 750 mg, 775 mg, 800 mg, 825 mg, 850 mg, 875 mg, 900 mg, 925 mg, 950 mg, 975 mg, 1.0 g, 1.25 g, 1.50 g, 1.75 g, 2.0 g, 2.25 g, 2.50 g, 2.75 g, 3.0 g, 3.25 g, 3.50 g, 3.75 g, 4.0 g, 4.25 g, 4.50 g, 4.75 g, 5.0 g, 5.25 g, 5.50 g, 5.75 g, 6.0 g, 6.25 g, 6.50 g, 6.75 g, 7.0 g, 7.25 g, 7.50 g, 7.75 g, 8.0 g, 8.25 g, 8.50 g, 8.75 g, 9.0 g, 9.25 g, 9.50 g, 9.75 g, 10.0 g, or any range or amount in between any two of the preceding values and any other ranges or amounts disclosed herein.

As used herein, a "protoberberine composition" defines a composition comprising one or more of the following compounds: allocryptopine, berberine, berberine hydrochloride, canadine, columbamine, coptisine, cordylamine, corysamine, cryptopine, cyclanoline, dihydroberberine, dihydrocoptisine, dihydropalmatine, epiberberine, groenlandicine, jatrorrhizine, methyl stepholidine, palmatine, protopine, pseudoberberine, pseudocoptisine, scoulerine, stepharanine, stepholidine, stylopine, tetrahydroberberine, and tetrahydropalmatine.

When provided in a DPP-4 inhibitor composition, the amount of a protoberberine composition provided may be about 10 μg to about 10 g. For example, the amount of a protoberberine composition in the DPP-4 inhibitor composition can be about 10 μg, 15 μg, 20 μg, 25 μg, 30 μg, 35 μg, 40 μg, 45 μg, 50 μg, 55 μg, 60 μg, 65 μg, 70 μg, 75 μg, 80 μg, 85 μg, 90 μg, 95 μg, 100 μg, 125 μg, 150 μg, 175 μg, 200 μg, 225 μg, 250 μg, 275 μg, 300 μg, 325 μg, 350 μg, 375 μg, 400 μg, 425 μg, 450 μg, 475 μg, 500 μg, 525 μg, 550 μg, 575 μg, 600 μg, 625 μg, 650 μg, 675 μg, 700 μg, 725 μg, 750 μg, 775 μg, 800 μg, 825 μg, 850 μg, 875 μg, 900 μg, 925 μg, 950 μg, 975 μg, 1000 μg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 125 mg, 150 mg, 175 mg, 200 mg, 225 mg, 250 mg, 275 mg, 300 mg, 325 mg, 350 mg, 375 mg, 400 mg, 425 mg, 450 mg, 475 mg, 500 mg, 525 mg, 550 mg, 575 mg, 600 mg, 625 mg, 650 mg, 675 mg, 700 mg, 725 mg, 750 mg, 775 mg, 800 mg, 825 mg, 850 mg, 875 mg, 900 mg, 925 mg, 950 mg, 975 mg, 1.0 g, 1.25 g, 1.50 g, 1.75 g, 2.0 g, 2.25 g, 2.50 g, 2.75 g, 3.0 g, 3.25 g, 3.50 g, 3.75 g, 4.0 g, 4.25 g, 4.50 g, 4.75 g, 5.0 g, 5.25 g, 5.50 g, 5.75 g, 6.0 g, 6.25 g, 6.50 g, 6.75 g, 7.0 g, 7.25 g, 7.50 g, 7.75 g, 8.0 g, 8.25 g, 8.50 g, 8.75 g, 9.0 g, 9.25 g, 9.50 g, 9.75 g, 10.0 g, or any range or amount in between any two of the preceding values and any other ranges or amounts disclosed herein.

As used herein, a "pharmaceutical DPP composition" defines a composition comprising one or more of sitagliptin, vildagliptin, saxagliptin, linagliptin, gemigliptin, anagliptin, teneligliptin, alogliptin, trelagliptin, and omarigliptin.

When provided in a DPP-4 inhibitor composition, the amount of a pharmaceutical DPP composition provided may be about 0.5 mg to about 200 mg. For example, the amount of a pharmaceutical GLP composition in the DPP-4 inhibitor composition can be about 0.5 mg, 1 mg, 1.5 mg, 2 mg, 2.5 mg, 3 mg, 3.5 mg, 4 mg, 4.5 mg, 5 mg, 5.5 mg, 6 mg, 6.5 mg, 7 mg, 7.5 mg, 8 mg, 8.5 mg, 9 mg, 9.5 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 30 mg, 35 mg, 40 mg, 45 mg, 50 mg, 55 mg, 60 mg, 65 mg, 70 mg, 80 mg, 85 mg, 90 mg, 95 mg, 100 mg, 110 mg, 120 mg, 130 mg, 140 mg, 150 mg, 160 mg, 170 mg, 180 mg, 190 mg, 200 mg, or any range or amount in between any two of the preceding values and any other ranges or amounts disclosed herein.

As used herein, a hydroxycitric acid composition, an EGCG composition, a sucralose composition, a bayberry powder composition, a camellia sinensis (matcha) powder composition, a lion's mane mushroom powder composition, a uva ursi leaf powder composition, a capsaicin (chili pepper) composition, a curcumin composition, a freeze dried milk (Kefir Powder) composition, a medium chain triglyc- erides composition, and a conjugated linoleic acid compo- sition are defined as above. When provided in a DPP-4 inhibitor composition, the amount of these compositions independently may be about 10 µg to about 10 g, such as about 10 µg, 15 µg, 20 µg, 25 µg, 30 µg, 35 µg, 40 µg, 45 µg, 50 µg, 55 µg, 60 µg, 65 µg, 70 µg, 75 µg, 80 µg, 85 µg, 90 µg, 95 µg, 100 µg, 125 µg, 150 µg, 175 µg, 200 µg, 225 µg, 250 µg, 275 µg, 300 µg, 325 µg, 350 µg, 375 µg, 400 µg, 425 µg, 450 µg, 475 µg, 500 µg, 525 µg, 550 µg, 575 µg, 600 µg, 625 µg, 650 µg, 675 µg, 700 µg, 725 µg, 750 µg, 775 µg, 800 µg, 825 µg, 850 µg, 875 µg, 900 µg, 925 µg, 950 µg, 975 µg, 1000 µg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 125 mg, 150 mg, 175 mg, 200 mg, 225 mg, 250 mg, 275 mg, 300 mg, 325 mg, 350 mg, 375 mg, 400 mg, 425 mg, 450 mg, 475 mg, 500 mg, 525 mg, 550 mg, 575 mg, 600 mg, 625 mg, 650 mg, 675 mg, 700 mg, 725 mg, 750 mg, 775 mg, 800 mg, 825 mg, 850 mg, 875 mg, 900 mg, 925 mg, 950 mg, 975 mg, 1.0 g, 1.25 g, 1.50 g, 1.75 g, 2.0 g, 2.25 g, 2.50 g, 2.75 g, 3.0 g, 3.25 g, 3.50 g, 3.75 g, 4.0 g, 4.25 g, 4.50 g, 4.75 g, 5.0 g, 5.25 g, 5.50 g, 5.75 g, 6.0 g, 6.25 g, 6.50 g, 6.75 g, 7.0 g, 7.25 g, 7.50 g, 7.75 g, 8.0 g, 8.25 g, 8.50 g, 8.75 g, 9.0 g, 9.25 g, 9.50 g, 9.75 g, 10.0 g, or any range or amount in between any two of the preceding values and any other ranges or amounts disclosed herein.

It is understood that DPP-4 inhibitors in a DPP-4 inhibitor composition described herein are not limited to the compo- sitions set forth above and any foods, nutrients, botanicals, and supplements inhibiting DPP-4 can also be included in a DPP-4 inhibitor composition. It is also understood that some compositions may have dule effects, i.e., being a GLP-1R agonist and a DPP-4 inhibitor.

In some embodiments, one or more compounds compris- ing a DPP-4 inhibitor composition, as described herein, may be formulated to be able to cross the blood brain barrier of a subject following administration of one or more DPP-4 inhibitor compositions as set forth herein. By providing at least one compound that is formulated to cross the blood brain barrier in the DPP-4 inhibitor composition a more robust patient outcome, i.e., increased weight loss, boosted satiety, and/or increased GLP-1 levels, can be observed in a subject. Without being bound by any particular theory, it is believed that GLP-1, an endogenous GLP-1R agonist, is secreted from intestinal L-cells and neurons. Because DPP-4 degrades GLP-1, providing a DPP-4 inhibitor composition reduces the degradation of GLP-1. Further, because a por- tion of endogenous GLP-1 originates from the brain, pro- viding DPP-4 inhibitors that can cross the blood brain barrier reduces the amount of GLP-1 that is degraded in the brain, which increases the global GLP-1 levels in a subject compared to DPP-4 inhibitors that do not cross the blood brain barrier. Accordingly, because more GLP-1 is circulat- ing in the body, the effects of having higher levels of GLP-1, i.e., increased weight loss and boosted satiety, are further improved.

Certain embodiments provide a combination composition comprising an amount of a GLP-1R agonist composition, as described herein, and an amount of a DPP-4 inhibitor composition, as described herein, wherein the amount of a GLP-1R agonist composition and the amount of a DPP-4 inhibitor composition are present in a ratio. In some embodi- ments, the ratio of the amount of a GLP-1R agonist com- position to the amount of a DPP-4 inhibitor composition may be about 1:1. In certain embodiments, the ratio of the amount of a GLP-1R agonist composition to the amount of a DPP-4 inhibitor composition can be within the range of about 10:1 to about 1:10. In this regard, the ratio of the amount of a GLP-1R agonist composition to the amount of a DPP-4 inhibitor composition may be about 10:1, 9.5:1, 9:1, 8.5:1, 8:1, 7.5:1, 7:1, 6.5:1, 6:1, 5.5:1, 5:1, 4.5:1, 4:1, 3.5:1, 3:1, 2.5:1, 2:1, 1.5:1, 1:1, 1:1.5, 1:2, 1:2.5, 1:3, 1:3.5, 1:4, 1:4.5, 1:5, 1:5.5, 1:6, 1:6.5, 1:7, 1:7.5, 1:8, 1:8.5, 1:9, 1:9.5, 1:10, or any ratio therebetween.

In some embodiments, the ratio of the amount of a GLP-1R agonist composition and the amount of a DPP-4 inhibitor composition present in a combination composition, as described herein, may be a synergistic ratio. As used herein, a "synergistic ratio" refers to a ratio that elicits an unexpectedly superior pharmacological, physiological, nutritional, or nutraceutical effect in a subject compared to conventional compositions. In some embodiments, the syn- ergistic ratio of the amount of a GLP-1R agonist composi- tion to the amount of a DPP-4 inhibitor composition may be about 1:1. In certain embodiments, the synergistic ratio of the amount of a GLP-1R agonist composition to the amount of a DPP-4 inhibitor composition can be within the range of about 5:1 to about 1:5. In this regard, the synergistic ratio of the amount of a GLP-1R agonist composition to the amount of a DPP-4 inhibitor composition may be about 5:1, 4.5:1, 4:1, 3.5:1, 3:1, 2.5:1, 2:1, 1.5:1, 1:1, 1:1.5, 1:2, 1:2.5, 1:3, 1:3.5, 1:4, 1:4.5, 1:5, or any ratio therebetween. In certain embodiments, a combination composition comprising a syn- ergistic ratio, as described herein, may elicit unexpectedly superior effects in increasing weight loss, boosting satiety, and/or increasing GLP-1 levels in a subject.

Without being bound by any particular theory, it is believed that providing a combination of a GLP-1R agonist composition and a DPP-4 inhibitor composition elicits a synergistic response for increasing weight loss, boosting satiety, and/or increasing GLP-1 levels in a subject. GLP-1R agonist compositions described herein can be formulated to decrease blood glucose levels following a meal by augment- ing the secretion of insulin and inhibiting the release of glucagon and may also boost satiety, thus reducing food intake. DPP-4 inhibitor compositions can be formulated to reduce the degradation of GLP-1, and similar GLP-1R agonists. Accordingly, by providing a GLP-1R agonist composition and a DPP-4 inhibitor composition together, the concentration of GLP-1 and other GLP-1R agonists in a subject will remain at a higher level for longer than the same absent a DPP-4 inhibitor in an unexpectedly superior way. Accordingly, because the concentration of GLP-1 and other GLP-1R agonists becomes higher in a subject following administration of compositions described herein, the beneficial effects of having higher levels of GLP-1 and other GLP-1R agonists, i.e., increased weight loss and boosted satiety, are further improved and unexpectedly superior compared to either compound administered independently.

As described herein, a GLP-1R agonist composition and a DPP-4 inhibitor composition, whether provided in a combination composition or independently confer significant advantages over conventional GLP-1R agonists and DPP-4 inhibitors. The GLP-1R agonist compositions and DPP-4 inhibitor compositions disclosed herein can beneficially be produced using methods and costs that are significantly lower than those known in the art, along with conferring other advantages such as reducing manufacturing challenges, waste disposal, and avoidance of harmful chemicals in the manufacturing process. Additionally, the GLP-1R agonist compositions and DPP-4 inhibitor compositions disclosed herein have at most an equal, or more preferably a reduced, incidence of negative side effects compared to compositions known in the art and confer additional benefits as set forth herein and those envisaged by the skilled artisan in view of the instant disclosure.

In some embodiments, a GLP-1R agonist composition, as described herein, a DPP-4 inhibitor composition, as described herein, or a combination composition, as described herein, can comprise an amount of one or more supplement ingredients. As used herein, the term "supplement ingredient" can refer to essential fatty acids such as linolenic acid and linoleic acid, and essential amino acids such as tryptophan, lysine, methionine, phenylalanine, threonine, valine, leucine, isoleucine, arginine, and histidine, and n-acetyl cysteine. Also included within the meaning of supplement ingredients are vitamins such as retinol (vitamin A), thiamine (vitamin B1), riboflavin (vitamin B2), niacin (vitamin B3), pantothenic acid (vitamin B5), pyridoxine, pyridoxamine, or pyridoxal (vitamin B6), biotin (vitamin B7) or pharmaceutically acceptable salts thereof, folic acid (vitamin B9) or pharmaceutically acceptable salts thereof, cobalamin (vitamin B12), choline, ascorbic acid (vitamin C) or pharmaceutically acceptable salts thereof, ergocalciferol (vitamin D2), calciferol (vitamin D3), 22-dihydroergocalciferol (vitamin D4), sitocalciferol (vitamin D5), tocopherol (vitamin E), phylloquinone (vitamin K1), menaquinone (vitamin K2), menadione (vitamin K3), or any combination of the foregoing. Other vitamins not explicitly listed would readily be envisaged by those of skill in the art, in view of the disclosure contained herein. Supplement ingredients can further include dietary minerals such as, for example, chromium, bromine, cobalt, copper, fluorine, germanium, iodine, iron, magnesium, manganese, molybdenum, potassium, selenium, silicon, zinc, calcium, phosphorous, sodium, sulfur, and vanadium. Supplement ingredients can also comprise cranberry extract, turmeric, royal jelly, açaí berry, beet root, coral calcium, oyster shell, gotu kola, *Gingko biloba*, lions mane mushroom, pomegranate, hibiscus flower, strawberry powder, dandelion root, celery powder, parsley powder, peppermint leaf, cinnamon bark powder, maca root, nicotinamide riboside, NAD+ precursors, Coenzyme Q10, omega-3-fatty acids, cabbage powder, nicotinamide mononucleotide, and combinations thereof. Supplement ingredients can include nitrates such as citrulline nitrate, creatine nitrate, beta-alanine nitrate, and any other compound, such as a vitamin, a mineral, an herb, a botanical, an amino acid, an enzyme, a probiotic, etc., that is not explicitly listed above. Supplement ingredients also define any concentrates, metabolites, constituents, or extracts of any of the foregoing, and generally refer to any compound that is intended to supplement the diet of an individual. One skilled in the art would readily envisage the scope of compounds encompassed by the term "supplement ingredients," as that term is used herein. Compositions described herein can include one or more of the foregoing supplement ingredients, as would be understood by one of skill in the art.

Compositions described herein can comprise an amount of one or more supplement ingredients, which may be about 10 µg, 15 µg, 20 µg, 25 µg, 30 µg, 35 µg, 40 µg, 45 µg, 50 µg, 55 µg, 60 µg, 65 µg, 70 µg, 75 µg, 80 µg, 85 µg, 90 µg, 95 µg, 100 µg, 125 µg, 150 µg, 175 µg, 200 µg, 225 µg, 250 µg, 275 µg, 300 µg, 325 µg, 350 µg, 375 µg, 400 µg, 425 µg, 450 µg, 475 µg, 500 µg, 525 µg, 550 µg, 575 µg, 600 µg, 625 µg, 650 µg, 675 µg, 700 µg, 725 µg, 750 µg, 775 µg, 800 µg, 825 µg, 850 µg, 875 µg, 900 µg, 925 µg, 950 µg, 975 µg, 1000 µg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 125 mg, 150 mg, 175 mg, 200 mg, 225 mg, 250 mg, 275 mg, 300 mg, 325 mg, 350 mg, 375 mg, 400 mg, 425 mg, 450 mg, 475 mg, 500 mg, 525 mg, 550 mg, 575 mg, 600 mg, 625 mg, 650 mg, 675 mg, 700 mg, 725 mg, 750 mg, 775 mg, 800 mg, 825 mg, 850 mg, 875 mg, 900 mg, 925 mg, 950 mg, 975 mg, 1.0 g, or any range or amount in between.

In some embodiments, a GLP-1R agonist composition, as described herein, a DPP-4 inhibitor composition, as described herein, or a combination composition, as described herein, may further comprise an amount of at least one excipient. The excipients are not particularly limited. Exemplary excipients include, but are not limited to: acidifying agents (acetic acid, glacial acetic acid, citric acid, fumaric acid, hydrochloric acid, diluted hydrochloric acid, malic acid, nitric acid, phosphoric acid, diluted phosphoric acid, sulfuric acid, tartaric acid); alkalizing agents (ammonia solution, ammonium carbonate, diethanolamine, diisopropanolamine, potassium hydroxide, sodium bicarbonate, sodium borate, sodium carbonate, sodium hydroxide, trolamine); antifoaming agents (dimethicone, simethicone); antimicrobial preservatives (benzalkonium chloride, benzalkonium chloride solution, benzethonium chloride, benzoic acid, benzyl alcohol, butylparaben, cetylpyridinium chloride, chlorobutanol, chlorocresol, cresol, dehydroacetic acid, ethylparaben, methylparaben, methylparaben sodium, phenol, phenylethyl alcohol, phenylmercuric acetate, phenylmercuric nitrate, potassium benzoate, potassium sorbate, propylparaben, propylparaben sodium, sodium benzoate, sodium dehydroacetate, sodium propionate, sorbic acid, thimerosal, thymol); antioxidants (ascorbic acid, ascorbyl palmitate, butylated hydroxyanisole, butylated hydroxytoluene, hypophosphorous acid, monothioglycerol, propyl gallate, sodium formaldehyde sulfoxylate, sodium metabisulfite, sodium thiosulfate, sulfur dioxide, tocopherol, tocopherols excipient); buffering agents (acetic acid, ammonium carbonate, ammonium phosphate, boric acid, citric acid, lactic acid, phosphoric acid, potassium citrate, potassium metaphosphate, potassium phosphate monobasic, sodium acetate, sodium citrate, sodium lactate solution, dibasic sodium phosphate, monobasic sodium phosphate);

chelating agents (edetate disodium, ethylenediaminetetraacetic acid and salts, edetic acid); coating agents (sodium carboxymethylcellulose, cellulose acetate, cellulose acetate phthalate, ethylcellulose, gelatin, pharmaceutical glaze, hydroxypropyl cellulose, hydroxypropyl methylcellulose, hydroxypropyl methylcellulose phthalate, methacrylic acid copolymer, methylcellulose, polyvinyl acetate phthalate, shellac, sucrose, titanium dioxide, carnauba wax, microcrystalline wax, zein); colorants (caramel, red, yellow, black or blends, ferric oxide); complexing agents (ethylenediaminetetraacetic acid and salts (EDTA), edetic acid, gentisic acid ethanolamide, oxyquinoline sulfate); desiccants (calcium chloride, calcium sulfate, silicon dioxide); emulsifying and/or solubilizing agents (acacia, cholesterol, diethanolamine (adjunct), glyceryl monostearate, lanolin alcohols, mono- and di-glycerides, monoethanolamine (adjunct), lecithin, oleic acid (adjunct), oleyl alcohol (stabilizer), poloxamer, polyoxyethylene 50 stearate, polyoxyl 35 castor oil, polyoxyl 40 hydrogenated castor oil, polyoxyl 10 oleyl ether, polyoxyl 20 cetostearyl ether, polyoxyl 40 stearate, polysorbate 20, polysorbate 40, polysorbate 60, polysorbate 80, diacetate, monostearate, sodium lauryl sulfate, sodium stearate, sorbitan monolaurate, sorbitan monooleate, sorbitan monopalmitate, sorbitan monostearate, stearic acid, trolamine, emulsifying wax); filtering aids (powdered cellulose, purified siliceous earth); flavors and perfumes (anethole, benzaldehyde, ethyl vanillin, menthol, methyl salicylate, monosodium glutamate, orange flower oil, peppermint, peppermint oil, peppermint spirit, rose oil, stronger rose water, thymol, tolu balsam tincture, vanilla, vanilla tincture, vanillin); humectants (glycerol, hexylene glycol, sorbitol); plasticizers (castor oil, diacetylated monoglycerides, diethyl phthalate, glycerol, mono- and di-acetylated monoglycerides, propylene glycol, triacetin, triethyl citrate); polymers (cellulose acetate, alkyl celluloses, hydroxyalkyl, acrylic polymers and copolymers); solvents (acetone, alcohol, diluted alcohol, amylene hydrate, benzyl benzoate, butyl alcohol, carbon tetrachloride, chloroform, corn oil, cottonseed oil, ethyl acetate, glycerol, hexylene glycol, isopropyl alcohol, methyl alcohol, methylene chloride, methyl isobutyl ketone, mineral oil, peanut oil, propylene carbonate, sesame oil, water for injection, sterile water for injection, sterile water for irrigation, purified water); sorbents (powdered cellulose, charcoal, purified siliceous earth); carbon dioxide sorbents (barium hydroxide lime, soda lime); stiffening agents (hydrogenated castor oil, cetostearyl alcohol, cetyl alcohol, cetyl esters wax, hard fat, paraffin, polyethylene excipient, stearyl alcohol, emulsifying wax, white wax, yellow wax); suspending and/or thickening agents (acacia, agar, alginic acid, aluminum monostearate, bentonite, purified bentonite, magma bentonite, carbomer, carboxymethylcellulose calcium, carboxymethylcellulose sodium, carboxymethylcellulose sodium 12, carrageenan, microcrystalline and carboxymethylcellulose sodium cellulose, dextrin, gelatin (Bloom strength 50-100), guar gum, hydroxyethyl cellulose, hydroxypropyl cellulose, hydroxypropyl methylcellulose, magnesium aluminum silicate, methylcellulose, pectin, polyethylene oxide, polyvinyl alcohol, povidone, alginate, silicon dioxide, colloidal silicon dioxide, sodium alginate, tragacanth, xanthan gum); sweetening agents (aspartame, dextrates, dextrose, excipient dextrose, fructose, mannitol, saccharin, calcium saccharin, sodium saccharin, sorbitol, solution sorbitol, sucrose, compressible sugar, confectioner's sugar, syrup); surfactants (simethicone); tablet binders (acacia, alginic acid, sodium carboxymethylcellulose, microcrystalline cellulose, dextrin, ethylcellulose, gelatin, liquid glucose, guar gum, hydroxypropyl methylcellulose, methylcellulose, polyethylene oxide, povidone, pregelatinized starch, syrup); tablet and/or capsule diluents (calcium carbonate, dibasic calcium phosphate, tribasic calcium phosphate, calcium sulfate, microcrystalline cellulose, powdered cellulose, dextrates, dextrin, dextrose excipient, fructose, kaolin, lactose, mannitol, sorbitol, starch, pregelatinized starch, sucrose, compressible sugar, confectioner's sugar); tablet disintegrants (alginic acid, microcrystalline cellulose, croscarmellose sodium, crospovidone, polacrilin potassium, sodium starch glycolate, starch, pregelatinized starch); tablet and/or capsule lubricants (calcium stearate, glyceryl behenate, magnesium stearate, light mineral oil, sodium stearyl fumarate, stearic acid, purified stearic acid, talc, hydrogenated vegetable oil, zinc stearate); tonicity agent (dextrose, glycerol, mannitol, potassium chloride, sodium chloride); vehicle: flavored and/or sweetened (aromatic elixir, compound benzaldehyde elixir, iso-alcoholic elixir, peppermint water, sorbitol solution, syrup, tolu balsam syrup); vehicle: oleaginous (almond oil, corn oil, cottonseed oil, ethyl oleate, isopropyl myristate, isopropyl palmitate, mineral oil, light mineral oil, myristyl alcohol, octyl dodecanol, olive oil, peanut oil, persic oil, sesame oil, soybean oil, squalane); vehicle: solid carrier (sugar spheres); vehicle: sterile (Bacteriostatic water for injection, bacteriostatic sodium chloride injection); water repelling agents (cyclomethicone, dimethicone, simethicone); and/or solubilizing agent (benzalkonium chloride, benzethonium chloride, cetylpyridinium chloride, docusate sodium, nonoxynol 9, nonoxynol 10, octoxynol 9, poloxamer, polyoxyl 35 castor oil, polyoxyl 40, hydrogenated castor oil, polyoxyl 50 stearate, polyoxyl 10 oleyl ether, polyoxyl 20 cetostearyl ether, polyoxyl 40 stearate, polysorbate 20, polysorbate 40, polysorbate 60, polysorbate 80, sodium lauryl sulfate, sorbitan monolaurate, sorbitan monooleate, sorbitan monopalmitate, sorbitan monostearate, tyloxapol). This list is not meant to be exclusive, but instead merely representative of the classes of excipients and the particular excipients that may be used in a GLP-1R agonist composition, as described herein, a DPP-4 inhibitor composition, as described herein, or a combination composition, as described herein.

The compounds comprising a GLP-1R agonist composition, as described herein, a DPP-4 inhibitor composition, as described herein, or a combination composition, as described herein, may comprise one or more active agents in a therapeutically effective amount. By way of example, a "therapeutically effective amount" and/or an "effective amount" of the compound disclosed herein can be (on a dosage weight per subject weight basis), for example, 0.1 µg/kg, 0.5 µg/kg, 1 µg/kg, 1.5 µg/kg, 2.0 µg/kg, 2.5 µg/kg, 3.0 µg/kg, 3.5 µg/kg, 4.0 µg/kg, 4.5 µg/kg, 5.0 µg/kg, 10 µg/kg, 15 µg/kg, 20 µg/kg, 25 µg/kg, 30 µg/kg, 35 µg/kg, 40 µg/kg, 45 µg/kg, 50 µg/kg, 55 µg/kg, 60 µg/kg, 65 µg/kg, 70 µg/kg, 75 µg/kg, 80 µg/kg, 85 µg/kg, 90 µg/kg, 95 µg/kg, 100 µg/kg, 150 µg/kg, 200 µg/kg, 250 µg/kg, 300 µg/kg, 350 µg/kg, 400 µg/kg, 450 µg/kg, 500 µg/kg, 550 µg/kg, 600 µg/kg, 650 µg/kg, 700 µg/kg, 750 µg/kg, 80 µg/kg 0, 850 µg/kg, 900 µg/kg, 1 mg/kg, 1.5 mg·kg, 2.0 mg/kg, 2.5 mg/kg, 3 mg/kg, 3.5 mg/kg, 4.0 mg/kg, 4.5 mg/kg, 5 mg/kg, 5.5 mg/kg, 6 mg/kg, 6.5 mg/kg, 7 mg/kg, 7.5 mg/kg, 8 mg/kg, 8.5 mg/kg, 9 mg/kg, 9.5 mg/kg, 10 mg/kg 10.5 mg/kg, 11 mg/kg, 11.5 mg/kg, 12 mg/kg, 12.5 mg/kg, 13 mg/kg, 13.5 mg/kg, 14 mg/kg, 14.5 mg/kg, 15 mg/kg, 16 mg/kg, 17 mg/kg, 18 mg/kg, 19 mg/kg, 20 mg/kg, 21 mg/kg, 22 mg/kg, 23 mg/kg, 24 mg/kg, 25 mg/kg, 30 mg/kg, 35 mg/kg, 40 mg/kg, 45 mg/kg, 50 mg/kg, 55 mg/kg, 60 mg/kg, 65 mg/kg, 70 mg/kg, or more, or any fraction or integer in between any two of the preceding amounts of the compound. An effective amount may include any of the ranges and amounts discussed herein.

Accordingly, in some embodiments, the dose of the compositions disclosed herein (corresponding to the therapeutically effective amount), can be about 10 µg to about 10 g per day. For example, the amount of the composition can be 10 µg, 15 µg, 20 µg, 25 µg, 30 µg, 35 µg, 40 µg, 45 µg, 50 µg, 55 µg, 60 µg, 65 µg, 70 µg, 75 µg, 80 µg, 85 µg, 90 µg, 95 µg, 100 µg, 125 µg, 150 µg, 175 µg, 200 µg, 225 µg, 250 µg, 275 µg, 300 µg, 325 µg, 350 µg, 375 µg, 400 µg, 425 µg, 450 µg, 475 µg, 500 µg, 525 µg, 550 µg, 575 µg, 600 µg, 625 µg, 650 µg, 675 µg, 700 µg, 725 µg, 750 µg, 775 µg, 800 µg, 825 µg, 850 µg, 875 µg, 900 µg, 925 µg, 950 µg, 975 µg, 1000 µg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 125 mg, 150 mg, 175 mg, 200 mg, 225 mg, 250 mg, 275 mg, 300 mg, 325 mg, 350 mg, 375 mg, 400 mg, 425 mg, 450 mg, 475 mg, 500 mg, 525 mg, 550 mg, 575 mg, 600 mg, 625 mg, 650 mg, 675 mg, 700 mg, 725 mg, 750 mg, 775 mg, 800 mg, 825 mg, 850 mg, 875 mg, 900 mg, 925 mg, 950 mg, 975 mg, 1.0 g, 1.25 g, 1.50 g, 1.75 g, 2.0 g, 2.25 g, 2.50 g, 2.75 g, 3.0 g, 3.25 g, 3.50 g, 3.75 g, 4.0 g, 4.25 g, 4.50 g, 4.75 g, 5.0 g, 5.25 g, 5.50 g, 5.75 g, 6.0 g, 6.25 g, 6.50 g, 6.75 g, 7.0 g, 7.25 g, 7.50 g, 7.75 g, 8.0 g, 8.25 g, 8.50 g, 8.75 g, 9.0 g, 9.25 g, 9.50 g, 9.75 g, 10.0 g, or more, or any range or amount in between any two of the preceding values and any other ranges or amounts disclosed herein.

In some embodiments, compositions, as described herein, can be administered via methods described elsewhere herein on an hourly basis, e.g., every one, two, three, four, five, six, seven, eight, nine, ten, eleven, twelve, thirteen, fourteen, fifteen, sixteen, seventeen, eighteen, nineteen, twenty, twenty-one, twenty-two, twenty-three hours, or any interval in between, or on a daily basis, every two days, every three days, every four days, every five days, every six days, every week, every eight days, every nine days, every ten days, every two weeks, every month, or more or less frequently, as needed to achieve the desired therapeutic effect.

In some embodiments, a ramping administration protocol, i.e., where a subject is administered temporally increasing amounts of compositions described herein, can be utilized. For example, a subject could be administered with 100 mg of a composition, as described herein, once per day for 7 days, followed by 200 mg per day for the next 7 days, followed by 300 mg per day for the next 7 days. Administration protocols can also follow a pattern whereby the dosage amount decreases over time. For example, 300 mg of a composition, as described herein, per day for 7 days, followed by 200 mg per day for the next 7 days, followed by 100 mg per day for the next 7 days. In some embodiments, the methods as described herein can be utilized in combination with a calorie restriction protocol in a subject. In certain embodiments, the compositions described herein may be administered before, after, or during a meal. In addition, the appropriate dosage of the compositions can depend, for example, on the condition to be treated, the severity and course of the condition, whether the composition is administered for preventive or therapeutic purposes, previous therapy, the patient's clinical history and response to the composition, the type of composition used, and the discretion of the attending physician. The composition can be suitably administered to the patient at one time or over a series of treatments and may be administered to the patient at any time from diagnosis onwards. The composition may be administered to a subject as the sole composition. The composition may also be administered to a subject in conjunction with other drugs or therapies that were used or are currently used in treating the condition in question for many purposes, such as enhancing efficacy of these drugs or therapies, maintaining efficacy of these drugs or therapies whiling lowering their dosages and thus reducing potentially side effects associated therewith, or gradually allowing the subject to wean from these drugs or therapies to avoid potentially side effects associated therewith. Examples of these drugs or therapies include, but are not limited to, GLP-1 analogues (such as dulaglutide, albiglutide, exenatide, liraglutide, semaglutide, lixisenatide, and tirzepatide) and pharmaceutical DPP-4 inhibitors (such as sitagliptin, vildagliptin, saxagliptin, linagliptin, gemigliptin, anagliptin, teneligliptin, alogliptin, trelagliptin, and omarigliptin). The composition and one or more of these drugs or therapies can be delivered simultaneously, at different times, different frequency, and/or by different delivery routes or forms as set forth in this application.

In certain embodiments, a GLP-1R agonist composition, as described herein, a DPP-4 inhibitor composition, as described herein, or a combination composition, as described herein, can be formulated as a dietary supplement, nutritional supplement, or pharmaceutical agent.

In some embodiments, a GLP-1R agonist composition, as described herein, a DPP-4 inhibitor composition, as described herein, or a combination composition, as described herein, may be formulated to be administered via a route including, but not limited to buccally, interstitially, intramuscularly, intraperitoneally, intravenously, nasally, ophthalmically, orally, parenterally, rectally, subcutaneously, sublingually, or topically, and the like.

In certain embodiments, a GLP-1R agonist composition, as described herein, a DPP-4 inhibitor composition, as described herein, or a combination composition, as described herein, formulated to be administered via an oral route may be in the form of a powder, a granule, a suspension, an aqueous solution, an oil-based solution, a beverage, a syrup, an elixir, an emulsion, a capsule (soft, hard, gel, or plant-based), a pill, a tablet, a caplet, a sachet, a gum, or a dissolvable oral strip. In the aforementioned oral formulations, the formulation may comprise one or more of the aforementioned excipients. One skilled in the art would recognize the excipients appropriate for the particular oral delivery system contemplated. In addition, various methods of time release and location specific release are contemplated, including immediate release, delayed release, sustained release, controlled release, and targeted delivery.

Compositions intended for oral use can be prepared according to any method known in the art for the manufacture of pharmaceutically acceptable compositions and such compositions may include one or more of the following agents: sweeteners, flavoring agents, coloring agents, coatings, and preservatives. The sweetening and flavoring agents will increase the palatability of the preparation. Tablets containing the complexes in admixture with non-toxic pharmaceutically acceptable excipients suitable for tablet manufacture are acceptable. Pharmaceutically acceptable vehicles such as excipients are compatible with the other ingredients of the formulation (as well as non-injurious to the patient). Such excipients include inert diluents such as calcium carbonate, sodium carbonate, lactose, calcium phosphate or sodium phosphate; granulating and disintegrating agents, such as corn starch or alginic acid; binding agents such as starch, gelatin, or acacia; and lubricating agents such as magnesium stearate, stearic acid or talc. Tablets can be uncoated or can be coated by known techniques to delay disintegration and absorption in the gastrointestinal tract and thereby provide a sustained action over a longer period of time. For example, a time delay material such as glyceryl monostearate or glyceryl distearate alone or with a wax can be employed.

Formulations for oral use can also be presented as hard gelatin-containing or non-gelatinous capsules wherein the active ingredient is mixed with an inert solid diluent, for example calcium carbonate, calcium phosphate or kaolin, or as soft gelatin capsules wherein the active ingredient is mixed with water or an oil medium, such as peanut oil, liquid paraffin, or olive oil. Aqueous suspensions can contain the complex of the described herein admixed with excipients suitable for the manufacture of aqueous suspensions. Such excipients include suspending agents, dispersing, or wetting agents, one or more preservatives, one or more coloring agents, one or more flavoring agents and one or more sweetening agents such as sucrose or saccharin.

Oil suspensions can be formulated by suspending the active ingredient in a vegetable oil, such as arachis oil, olive oil, sesame oil or coconut oil, or in a mineral oil such as liquid paraffin. The oil suspension can contain a thickening agent, such as beeswax, hard paraffin or cetyl alcohol. Sweetening agents, such as those set forth above, and flavoring agents can be added to provide a palatable oral preparation. These compositions can be preserved by an added antioxidant such as ascorbic acid. Dispersible powders and granules suitable for preparation of an aqueous suspension by the addition of water can provide the active ingredient in admixture with a dispersing or wetting agent, a suspending agent, and one or more preservatives. Additional excipients, for example sweetening, flavoring, and coloring agents, can also be present.

Syrups and elixirs can be formulated with sweetening agents, such as glycerol, sorbitol, or sucrose. Such formulations can also contain a demulcent, a preservative, a flavoring, or a coloring agent.

Compositions formulated for parenteral administration can be in the form of a sterile injectable preparation, such as a sterile injectable aqueous or oleaginous suspension. This suspension can be formulated according to methods well known in the art using suitable dispersing or wetting agents and suspending agents. The sterile injectable preparation can also be a sterile injectable solution or suspension in a non-toxic parenterally-acceptable diluent or solvent, such as a solution in 1,3-butanediol. Suitable diluents include, for example, water, Ringer's solution, and isotonic sodium chloride solution. In addition, sterile fixed oils can be employed conventionally as a solvent or suspending medium. For this purpose, any bland fixed oil can be employed including synthetic monoglycerides or diglycerides. In addition, fatty acids such as oleic acid can likewise be used in the preparation of injectable preparations.

It will be appreciated that the amount of the composition may be combined with a carrier material to produce a single dosage form. Such forms will vary depending upon the host treated and the particular mode of administration.

Aqueous suspensions may contain the compound disclosed herein in admixture with excipients suitable for the manufacture of aqueous suspensions. Such excipients include suspending agents, dispersing, or wetting agents, one or more preservatives, one or more coloring agents, one or more flavoring agents and one or more sweetening agents such as sucrose or saccharin.

Utilization of controlled release vehicles would readily be envisaged by those of skill in the pharmaceutical sciences in view of the disclosure contained herein, and these aspects can be applied to nutritional and dietary supplements.

Numerous controlled release vehicles can be used, including biodegradable or bioerodable polymers such as polylactic acid, polyglycolic acid, and regenerated collagen. Controlled release drug delivery devices can include creams, lotions, tablets, capsules, gels, microspheres, liposomes, ocular inserts, minipumps, and other infusion devices such as pumps and syringes. Implantable or injectable polymer matrices, and transdermal formulations, from which active ingredients are slowly released, and can be used in the disclosed methods.

Controlled release preparations can be achieved by the use of polymers to form complexes with or absorb a composition, as described herein. The controlled delivery can be exercised by selecting appropriate macromolecules such as polyesters, polyamino acids, polyvinylpyrrolidone, ethylenevinyl acetate, methylcellulose, carboxymethylcellulose, and protamine sulfate, and the concentration of these macromolecule as well as the methods of incorporation are selected in order to control release of active complex.

Controlled release of compositions, as described herein, can be taken to mean any of the extended release dosage forms. The following terms may be considered to be substantially equivalent to controlled release for the purposes of the present disclosure: continuous release, controlled release, delayed release, depot, gradual release, long term release, programmed release, prolonged release, programmed release, proportionate release, protracted release, repository, retard, slow release, spaced release, sustained release, time coat, time release, delayed action, extended action, layered time action, long acting, prolonged action, sustained action medications and extended release, release in terms of pH level in the gut and intestine, breakdown of the molecule and based on the absorption and bioavailability.

Hydrogels, wherein a composition, as disclosed herein, is dissolved in an aqueous constituent to gradually release over time, can be prepared by copolymerization of hydrophilic mono-olefinic monomers, such as ethylene glycol methacrylate. Matrix devices, wherein a composition, as described herein, is dispersed in a matrix of carrier material, can be used. The carrier can be porous, non-porous, solid, semisolid, permeable, or impermeable. Alternatively, a device comprising a central reservoir of a composition disclosed herein surrounded by a rate controlling membrane can be used to control the release of the composition. Rate controlling membranes include ethylene-vinyl acetate copolymer or butylene terephthalate/polytetramethylene ether terephthalate. Use of silicon rubber or ethylene-vinyl alcohol depots are also contemplated.

Controlled release oral formulations can also be used. In some embodiments, a composition, as described herein, can be incorporated into a soluble or erodible matrix, such as a pill or a lozenge. In another example, the oral formulations can be a liquid used for sublingual administration. These liquid compositions can also be in the form a gel or a paste. Hydrophilic gums, such as hydroxymethylcellulose, can be used. A lubricating agent such as magnesium stearate, stearic acid, or calcium stearate can be used to aid in the tableting process.

In some embodiments, dosing for oral administration may be with a regimen calling for single daily dose, or for a single dose every other day, or for a single dose within 72 hours of the first administered dose, or for multiple, spaced doses throughout the day. The active compositions, which make up the therapy, may be administered simultaneously, either in a combined dosage form or in separate dosage forms intended for substantially simultaneous oral administration. The active compositions, which make up the therapy may also be administered sequentially, with either active composition being administered by a regimen calling for two-step ingestion. Thus, a regimen may call for sequential administration of the active compositions with spaced-apart ingestion of the separate, active compositions. The time period between the multiple ingestion steps may range from a few minutes to as long as about 72 hours, depending upon the properties of each active composition, such as potency, solubility, bioavailability, plasma half-life and kinetic profile of the composition, as well as depending upon the age and condition of the patient. The active compositions of the therapy whether administered simultaneously, substantially simultaneously, or sequentially, may involve a regimen calling for administration of one active composition by oral route and the other active composition by intravenous route. In one aspect, the embodiments described herein can achieve therapeutic and/or nutraceutical benefits not previously recognized or achievable, and thus, unexpectedly, and surprisingly achieve improved abilities for using the compositions. In some embodiments, a composition can be formulated for intravenous administration because a more concentrated solution can be produced. Whether the active compositions of the therapy are administered by oral or intravenous route, separately or together, each such active composition will be contained in a suitable pharmaceutical formulation of pharmaceutically-acceptable excipients, diluents, or other formulations components.

In certain embodiments, a combination composition comprising a GLP-1R agonist composition, as described herein, and a DPP-4 inhibitor composition, as described herein, may be formulated as a single dosage form intended for concurrent delivery of the GLP-1R agonist composition and the DPP-4 inhibitor composition. Neither the route of administration nor the particular dosage form utilized to achieve such are particularly limited and may be any route of administration or dosage form contemplated herein. As a non-limiting example, the GLP-1R agonist composition and the DPP-4 inhibitor composition may, for example, be formulated into a single capsule for oral administration to a subject.

In some embodiments, a combination composition comprising a GLP-1R agonist composition, as described herein, and a DPP-4 inhibitor composition, as described herein, may be formulated as a single dosage form intended to impart differential delivery kinetics of the compositions contained therein. Neither the route of administration nor the particular dosage form utilized to achieve such are particularly limited and may be any route of administration or dosage form contemplated herein. As a non-limiting example, the GLP-1R agonist composition and the DPP-4 inhibitor composition may, for example, be formulated into a single tablet, such that about half of the tablet comprises the GLP-1R agonist composition and the about other half of the tablet comprises the DPP-4 inhibitor composition, with an impermeable barrier provided therebetween, wherein the particular excipients, coatings, etc. used in each half of the tablet result in differential delivery kinetics. In certain instances, the dosage form may be formulated to release the GLP-1R agonist composition faster than the DPP-4 inhibitor composition. In other instances, the dosage form may be formulated to release the DPP-4 inhibitor composition faster than GLP-1R agonist composition. It is understood that the relative dosage timing and release profiles of GLP-1R agonists and DPP-4 inhibitors can affect the efficacy of their combined administration when administered to certain subjects because it is understood that DPP-4 can break down GLP-1, thereby inhibiting the efficacy of the GLP-1R agonist. Accordingly, certain embodiments synergistically optimize the timing and release profile of the GLP-1R agonist relative to the DPP-4 inhibitor to achieve unexpectedly superior results. In certain embodiments, a single dosage form can comprise a DPP-4 inhibitor composition in a regular-release formulation and a GLP-1R agonist composition in a controlled-release formulation. In certain embodiments, a single dosage form can comprise a DPP-4 inhibitor composition and a GLP-1R agonist composition both in controlled-release formulations wherein the GLP-1R agonist composition is released within about 0-10 minutes, within about 0-20 minutes, within about 0-30 minutes, within about 0-60 minutes within about 5-10 minutes, within about 10-20 minutes, within about 10-30 minutes, within about 20-30 minutes, within about 10-60 minutes, within about 20-40 minutes, within about 30-40 minutes, within about 40-60 minutes, within about 50-60 minutes, of releasing the DPP-4 inhibitor composition. In certain embodiments, a single dosage form comprising a DPP-4 inhibitor composition and a GLP-1R agonist composition can be administered solely or in conjunction with drugs or therapies that were used or are currently used in treating the condition in question to enhance efficacy of these drugs or therapies, maintain efficacy of these drugs or therapies with lower dosages and thus reduce potentially side effects associated with these drugs or therapies, or gradually allow a subject in need to wean from these drugs or therapies to avoid potentially side effects associated therewith. Examples of these drugs or therapies include, but are not limited to, one or more of GLP-1 analogues (such as dulaglutide, albiglutide, exenatide, liraglutide, semaglutide, lixisenatide, and tirzepatide) and one or more of pharmaceutical DPP-4 inhibitors (such as dulaglutide, albiglutide, exenatide, liraglutide, semaglutide, lixisenatide, and tirzepatide). In certain embodiments, a single dosage form comprising a DPP-4 inhibitor composition and a GLP-1R agonist composition can be co-administered to a subject with one or more of GLP-1 analogues simultaneously to lower dosages of the one or more of GLP-1 analogues for reduced side effects associated therewith and/or to allow the subject to gradually wean from the one or more of GLP-1 analogues. In certain embodiments, a single dosage form comprising a DPP-4 inhibitor composition and a GLP-1R agonist composition can be administered separately with one or more of GLP-1 analogues. For example, one or more of GLP-1 analogues may be administered first for a period of time to lose weight followed by administration of a single dosage form comprising a DPP-4 inhibitor composition and a GLP-1R agonist composition to prevent weight gain. As used herein, a period of time can be one day to one year or more depending on a subject's need and tolerance and can be readily envisaged by a skilled artisan.

In some embodiments, a combination composition comprising a GLP-1R agonist composition, as described herein, and a DPP-4 inhibitor composition, as described herein, may be formulated in a single dosage form, one or more dosage forms, and/or separate dosage forms intended for delivery of the GLP-1R agonist composition and the DPP-4 inhibitor composition. By formulating the GLP-1R agonist composition and DPP-4 inhibitor composition in separate dosage forms, a scheduled delivery scheme may be employed. In some embodiments, a scheduled delivery scheme may provide the GLP-1R agonist composition and the DPP-4 inhibitor composition concurrently to a subject. In other embodiments, a scheduled delivery scheme may provide the GLP-1R agonist composition and the DPP-4 inhibitor composition at different times, different frequency, and/or by different delivery routes or forms. Neither the route of administration nor the particular dosage form utilized to achieve such are particularly limited and may be any route of administration or dosage form contemplated herein. In certain embodiments, a DPP-4 inhibitor composition may be administered first followed by administration of a GLP-1R agonist composition, where the interval between the two administrations can be from about 15 minutes to 24 hours or any time in between. For example, the interval can be within 1 hour, between about 15 minutes to 30 minutes, about 20 minutes to 40 minutes, about 30 minutes to 1 hour, about 1 hour to 2 hours, about 2 hours to 3 hours, about 3 hours to 4 hours, about 4 hours to 5 hours, about 5 hours to 6 hours, about 6 hours to 7 hours, about 7 hours to 8 hours, about 8 hours to 9 hours, about 9 hours to 10 hours, about 10 hours to 11 hours, about 11 hours to 12 hours, about 12 hours to 13 hours, about 13 hours to 14 hours, about 14 hours to 15 hours, about 15 hours to 16 hours, about 16 hours to 17 hours, about 17 hour to 18 hours, about 18 hours to 19 hours, about 19 hours to 20 hours, about 20 hours to 21 hours, about 21 hours to 22 hours, about 22 hours to 23 hours, about 23 hours to 24 hours, about 2 hours to 4 hours, about 3 hours to 5 hours, about 4 hours to 8 hours, about 6 hours to 8 hours, about 7 hours to 12 hours, about 8 hours to 10 hours, about 12 hours to 14 hours, about 15 hours to 18 hours, and about 18 hours to 20 hours. In certain embodiments, a DPP-4 inhibitor composition may be administered after administration of a GLP-1R agonist composition, where the interval between the two administrations can be from about 1 minute to 1 hour or any time in between. For example, the interval can be between about 1 minute to 5 minutes, about 5 minutes to 10 minutes, about 10 minutes to 15 minutes, about 15 minutes to 30 minutes, about 20 minutes to 40 minutes, about 30 minutes to 45 minutes, about 40 minutes to 50 minutes, and about 45 minutes to 1 hour. In certain embodiments, a DPP-4 inhibitor composition may be administered once a day whereas a GLP-1R agonist composition may be administered several times a day. A DPP-4 composition, a GLP-1R agonist composition, or both can be taken with or without food. For example, A DPP-4 composition, a GLP-1R agonist composition, or both can be taken prior to a meal, with a meal, following a meal or anytime between meals. In some embodiments, the separate dosage forms may utilize the same route of administration; for example, the GLP-1R agonist composition may be formulated as a soft-gel capsule for oral administration and the DPP-4 inhibitor composition may be formulated as a tablet for oral administration, wherein both are administered to a subject simultaneously (for concurrent administration) or at separate times, e.g. a few hours apart. In other embodiments, the separate dosage forms may utilize different or mixed mode routes of administration; for example, the GLP-1R agonist composition may be formulated as an injection for subcutaneous administration and the DPP-4 inhibitor composition may be formulated as a tablet for oral administration, wherein both are administered to a subject simultaneously; which may or may not be concurrent delivery depending on the dosage form and route of administration used because of pharmacokinetic differences, i.e., some dosage forms (e.g., a delayed-release capsule vs. an instant release capsule) and administration routes (e.g., oral vs. subcutaneous) may take longer to elicit an effect.

To reduce the side effects of drugs or therapies that were used or are currently used in treating the condition in question (such as one or more of GLP-1 analogues and one or more of pharmaceutical DPP-4 inhibitors), a DPP-4 inhibitor composition and a GLP-1R agonist composition as described herein can be used in conjunction with the one or more of these drugs or therapies. For example, a DPP-4 inhibitor composition, a GLP-1R agonist composition, and one or more of GLP-1 analogues can be concurrently administered. In certain embodiments, a DPP-4 inhibitor composition, a GLP-1R agonist composition, and one or more of GLP-1 analogues can be cyclically administered. For example, the DPP-4 inhibitor composition is administered first for a period of time, followed by administration of the GLP-1R agonist composition, followed by administration of the one or more of GLP-1 analogues and so forth, and repeating this sequential administration. In certain embodiments, a subject can use a DPP-4 inhibitor composition and a GLP-1R agonist composition described herein to prevent weight gain after the subject has stopped taking one or more of GLP-1 analogues. For example, a subject can take one or more of GLP-1 analogues first to lose weight for a period of time and then switch to a DPP-4 inhibitor composition and/or a GLP-1R agonist composition, which can be administered either concurrently or at different times as set forth herein. As used herein, "a period of time" can be a single day, several days (such as 2 days, 3 days, 4 days, 5 days or more), and several months (such as 1 month, 2 months, 3 months, or more). The routes of administration for a DPP-4 inhibitor composition, a GLP-1R agonist composition, and one or more of other GLP-1 agonists can be the same and different. For example, the one or more of GLP-1 analogues can be injected subcutaneously while the DPP-4 inhibitor composition and the GLP-1R agonist composition can be administered orally.

In certain embodiments, a GLP-1R agonist composition, as described herein, a DPP-4 inhibitor composition, as described herein, a combination composition, as described herein, or any formulation thereof, may be administered to a subject to increase weight loss, boost satiety, increase GLP-1 levels, or any combination of the forgoing. In other embodiments, a GLP-1R agonist composition, as described herein, a DPP-4 inhibitor composition, as described herein, a combination composition, as described herein, or any formulation thereof, may be administered to a subject to treat, ameliorate, prevent, or reduce the risk of experiencing any disease, disorder, or condition including, but not limited to bladder cancer, breast cancer, cardiovascular disease, colorectal cancer, coronary heart disease, diabetic nephropathy, diabetic neuropathy, diabetic retinopathy, dyslipidemia, endometrial cancer, esophageal cancer, gallbladder cancer, gallbladder disease, gastric cancer, gastroparesis, hyperglycemia, hypertension, kidney cancer, liver cancer, lung cancer, meningioma, metabolic syndrome, multiple myeloma, obesity, osteoarthritis, ovarian cancer, pancreatic cancer, stroke, thyroid cancer, and type 2 diabetes mellitus.

In some embodiments, compositions described herein may be formulated as supplements or dosages designed for animals. In some animal applications, the compound or composition may be added to and/or comprise a pet treat or biscuit, for example, a dog biscuit or a cat treat.

The term "pharmaceutically acceptable salts" includes salts of the active compounds, which are prepared with relatively nontoxic acids or bases, depending on the particular substituents found on the compounds comprising the compositions described herein. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids, and the like, as well as the salts derived from relatively nontoxic organic acids like acetic acid, propionic acid, isobutyric acid, maleic acid, malonic acid, benzoic acid, succinic acid, suberic acid, fumaric acid, lactic acid, mandelic acid, phthalic acid, benzenesulfonic acid, p-tolylsulfonic acid, citric acid, tartaric acid, methanesulfonic acid, and the like. Also included are salts of amino acids such as arginate and the like, and salts of organic acids like glucuronic or galacturonic acids, and the like (see, for example, Berge et al., Journal of Pharmaceutical Science, 66: 1-19 (1977), which is hereby incorporated by reference in its entirety). Certain specific compounds of the present application contain both basic and acidic functionalities that allow the compounds to be converted into either base or acid addition salts.

As used herein, the term "pharmaceutically acceptable solvent" can refer to water or aqueous buffer solutions that are physiologically compatible, or aqueous solutions containing organic solvents that are physiologically compatible. A non-comprehensive list of pharmaceutically acceptable solvents is provided in U.S. Department of Health & Human Services, Food & Drug Administration, "Guidance for Industry: Q3C Impurities: Residual Solvents," December 1997 or its current issue.

The terms "dietary supplement," or "nutritional supplement" have the meaning ascribed to them under the Federal Food, Drug & Cosmetic Act.

As used herein, the term "excipient" refers to any compound that is part of a formulation that is not an active ingredient, i.e., one that has no relevant biological activity, and which is added to the formulation to provide specific characteristics to the dosage form, including by way of example, providing protection to the active ingredient from chemical degradation, facilitating release of a tablet or caplet from equipment in which it is formed, and so forth.

As used herein, the term "extract" means that the referenced compound can be physically or chemically altered to produce one or more compounds capable of being incorporated into the compositions described herein. For example, an extract can be a non-natural compound that is chemically distinct from that which exists in nature by virtue of subjecting a compound or raw material to human-controlled manufacturing or processing techniques, such as those described herein. In certain instances, an extract can refer to a non-natural composition that has had undesired components removed, thereby producing a compound that has markedly different characteristics from that which exists in nature or that possesses an enlarged function compared to natural compositions. In some instances, a composition described herein can deviate from any natural composition by virtue of being formulated into a non-natural combination of constituents, such as those described herein. As set forth herein, an extract can be formulated to specifically exclude particular constituents of a starting material along with specifically include constituents of a starting material.

The term "pharmaceutical formulation", "formulation", "composition," and the like can refer to preparations that are in such a form as to permit the biological activity of the active ingredients to be effective, and therefore may be administered to a subject for therapeutic use along with pharmaceutical, dietary, and/or nutritional supplement use. The meaning of these terms will be clear to the skilled artisan based upon the context in which they are used.

A "therapeutically effective amount," as used herein, includes within its meaning, a non-toxic but sufficient amount of a compound active ingredient or composition comprising the same for use in the embodiments disclosed herein to provide the desired therapeutic effect. Similarly, "an amount effective to" or "an effective amount," as used herein, includes within its meaning, a non-toxic but sufficient amount of a compound active ingredient or composition comprising the same to provide the desired effect. A "therapeutically effective amount" or an "effective amount" includes amounts of compounds that would not be achievable through a standard or natural diet, but requires supplementation and dosing, as described herein, to achieve specific, non-natural outcomes as set forth herein, along with expanded utilization of any compounds originating from or derived from natural sources. The exact amount of the active ingredient required may vary from subject to subject depending on factors such as the species being treated, the age and general condition of the subject, the severity of the condition being treated, the particular composition being administered, the weight of the subject, the mode of administration, and so forth. Thus, it may not always be possible to specify an exact "effective amount." However, for any given case, an appropriate "effective amount" may be determined by one of ordinary skill in the art in view of the disclosure contained herein.

As used herein, the term "bioavailability" refers to the amount of a substance that is absorbed by a subject and ultimately available for biological activity in a subject's tissue and cells.

As used herein, "identifying," refers to detecting or selecting a subject from a population of potential subjects, for example, to establish that a particular subject possesses certain properties or characteristics. "Identifying" may include, for example, self-identification, self-diagnosis, and diagnosis by a medical professional.

As used herein, the terms "preventing", "treating", "treatment," "alleviating," "ameliorating," and the like are used herein to generally refer to obtaining a desired pharmacological, physiological, nutritional, and/or nutraceutical effects, the scopes and meanings of which will be clear to the skilled artisan based upon the context in which these terms are used. The effect may be prophylactic in terms of preventing or partially preventing a disease, symptom, or condition thereof and/or may be therapeutic in terms of a partial or complete cure of a disease, condition, symptom, or adverse effect attributed to the disease. The term "treatment" as used herein encompasses any treatment of a disease in a mammal, particularly a human, and includes: (a) preventing the disease from occurring in a subject that may be predisposed to the disease but has not yet been diagnosed as having it; (b) inhibiting the disease or arresting its development; or (c) relieving the disease, causing regression of the disease and/or its symptoms, conditions, and co-morbidities. In some embodiments, a composition, as described herein, may be administered to maintain healthy levels of a certain condition or biomarker in a subject, such as for example maintaining a healthy level of mental acuity. As set forth herein, any composition that is administered to prevent, treat, alleviate, or ameliorate any condition, can also be administered to maintain a healthy level of a physiological or biological condition. In certain embodiments, a nutritional supplement is administered to maintain a healthy level of one or more of the conditions disclosed herein. The scope and meaning of "preventing," "treating," "treatment," "alleviating," "ameliorating," and "maintaining healthy levels of" would be immediately envisaged by the skilled artisan when viewing the term in the context of the disclosure and the claims.

As provided herein, the disclosure of a "ratio" of compounds and compositions corresponds to a ratio provided in terms of mass of the components present in the ratio.

When used in this disclosure, the phrase "consisting essentially of" is meant including any elements listed after the phrase and limited to other elements that do not interfere with or contribute to the activity or action specified in the disclosure for the listed elements. Thus, the phrase "consisting essentially of" indicates that the listed elements are required or mandatory, but that other elements are optional and can or cannot be present depending upon whether or not they affect the activity or action of the listed elements. For example, the use of a composition "consisting essentially of a composition" for the treatment of a particular disease or disorder, or the maintenance of a healthy condition, would exclude other ingredients that would materially alter the intended outcome of the composition.

As used herein, a composition that "substantially" comprises a compound means that the composition contains more than about 80% by weight, more preferably more than about 90% by weight, even more preferably more than about 95% by weight, and most preferably more than about 98% by weight of the compound.

To provide a more concise description, some of the quantitative expressions given herein are not qualified with the term "about." It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value.

In addition, the appropriate dosage of the compositions can depend, for example, on the condition to be treated, the severity and course of the condition, whether the composition is administered for preventive or therapeutic purposes, previous therapy, the patient's clinical history and response to the composition, the type of composition used, and the discretion of the attending physician. The composition can be suitably administered to the patient at one time or over a series of treatments and may be administered to the patient at any time from diagnosis onwards. The composition may be administered as the sole treatment or in conjunction with other drugs or therapies useful in treating the condition in question.

The present disclosure provides GLP-1R agonist compositions, DPP-4 inhibitor compositions, or a combination composition thereof as solid/liquid dosage forms. By providing such dosage forms the aforementioned compositions are present in an unnatural form, i.e., is presented in a supplement (e.g., in a pill or powder), that is different from that which occurs naturally, or the nutritional or dietary supplement results in unnatural supplementation that is unachievable through a non-supplemented diet.

EXAMPLES

Example 1

Various agents will be evaluated for their GLP-1R binding activities using a GLP-1R agonist assay. The agents will be conjugated linoleic acid, bayberry powder, berberine hydrochloride, camellia sinensis (matcha), capsaicin (chili pepper), dong quai root powder, epigallocatechin gallate (EGCG), freeze dried milk (Kefir Powder), garcinia cambogia extract (hydroxycitric acid), ginseng, lion's mane mushroom, longvida curcumin (containing 95% curcuminoids), medium chain triglycerides, pterostilbene, quercetin pure, resveratrol, sucralose, and uva ursi leaf powder. Each agent will be tested at concentrations of 200 ug/ml, 66.7 ug/ml, 22.22 ug/ml, 7.41 ug/ml, 2.47 ug/ml, and 0.82 ug/ml and each test will be conducted three times at each concentration. Fold-activation values of each agent at each concentration will be determined as compared to those of a control. Agents having fold-activation values higher than the control will be considered as a GLP-1R agonist.

Example 2

A study will be conducted to evaluate various agents for their DPP-4 in vitro inhibition activities using recombinant DPP4 enzyme and the colorimetric substrate Gly-Pro p-nitroanilide hydrochloride (Gly-Pro-NA). Sitagliptin and distilled water will be used respectively as a positive control and as a negative control. The agents will be hydroxycitric acid, epigallocatechin gallate (EGCG), resveratrol, sucralose, pterostilbene, bayberry powder, berberine hydrochloride powder, camellia sinensis (matcha) powder, lion's mane mushroom powder, uva ursi leaf powder, capsaicin, longvida curcumin, freeze dried milk (Kefir Powder), medium chain triglycerides, and conjugated linoleic acid. An aqueous solution of each hydroxycitric acid, epigallocatechin gallate (EGCG), resveratrol, sucralose, pterostilbene and sitagliptin (positive control) will be used in the study. Each of bayberry powder, berberine, camellia sinensis (matcha), lion's mane mushroom, and uva ursi leaf powder will be suspended in water, hydrated for 1 hour under gentle agitation, centrifugated, and filtrated, and the resultant aqueous solutions will be used in the study. Kefir powder will be suspended in water and filtered and the resultant aqueous solution will be used in the study. An ethanol solution of capsaicin will be used in the study. Conjugated linoleic acid will be dissolved in water (containing 1% TWEEN20) and diluted in sodium phosphate buffer (0.1 M, pH 7.0). Solutions of longvida curcumin and medium chain triglycerides will be prepared to allow each of these agents to have direct contact with the DPP4 enzyme in the assay.

The study will be carried out in 96-well microtiter plates. To each well, a recombinant DPP4 enzyme solution (50 μL, 2 mU/mL in 50 mmol/L Tris-HCl buffer, pH 8.0) will be added. Solutions of each agent, the positive control, and the negative control will be added into the resultant recombinant DPP4 enzyme solutions. To each mixture, a Gly-Pro-NA solution (40 μL, 0.26 mmol/L in HEPES buffer, pH 7.05) will be added to initiate an enzyme reaction. The plates will be placed in a plate reader set to determine the absorbance at 405 nm at 37° C. Kinetic readings will be conducted every 5 minutes from minute 0 to minute 60 (total 13 readings). Readings for each agent will be graphed as a dose response curve and an overlay graph showing the relative comparison between different agents.

Example 3

Male Wistar Albino/Sprague Dawley rats (age: 8 weeks, body weight (BW): 180±20 g) will be purchased from the Experimental Research Unit of Firat University (FUDAM) and housed at standard conditions (22.2° C., humidity, 55 5±5%) with food and water provided ad libitum. The Animal Experiments Local Ethics Committee of Firat University will be approved the study in accordance with Directive 2010/63/EU and ARRIVE principles.

After a one-week adaption period the animals will be divided into the groups as shown in Table 1. The diets for the control group and high fat diet groups are shown in Table 2.

TABLE 1

Experimental groups

| Group | HED dose | Rat dosage (mg/kg BW) (n = 7)* |
|---|---|---|
| Control | — | — |
| High fat diet (HFD) | — | — |
| HFD + Commercial GLP-1R Agonist | 7 mg semaglutide | 0.71 mg semaglutide |
| HFD + Commercial DPP-4 Inhibitor | 2.5 mg saxagliptin | 0.26 mg saxagliptin |
| HFD + Commercial Combination | 7 mg semaglutide 2.5 mg saxagliptin | 0.71 mg semaglutide 0.26 mg sitagliptin |
| HFD + Agonist-1 | 1000 mg ginseng | 102.8 mg ginseng |
| HFD + Agonist-2 | 600 mg curcumin | 61.7 mg curcumin |
| HFD + Inhibitor-1 | 1000 mg resveratrol | 102.8 mg resveratrol |
| HFD + Inhibitor-2 | 1000 mg pterostilbene | 102.8 mg pterostilbene |
| HFD + Inhibitor-3 | 1000 mg berberine | 102.8 mg berberine |
| HFD + Combination 1 | 1000 mg ginseng 1000 mg resveratrol | 102.8 mg ginseng 102.8 mg resveratrol |
| HFD + Combination 2 | 1000 mg ginseng 1000 mg pterostilbene | 102.8 mg ginseng 102.8 mg pterostilbene |
| HFD + Combination 3 | 1000 mg ginseng 1000 mg berberine | 102.8 mg ginseng 102.8 mg berberine |
| HFD + Combination 4 | 600 mg curcumin 1000 mg resveratrol | 61.7 mg curcumin 102.8 mg resveratrol |
| HFD + Combination 5 | 600 mg curcumin 1000 mg pterostilbene | 61.7 mg curcumin 102.8 mg pterostilbene |
| HFD + Combination 6 | 600 mg curcumin 1000 mg berberine | 61.7 mg curcumin 102.8 mg berberine |
| HFD + Combination 7 | 1000 mg ginseng 600 mg curcumin 1000 mg berberine | 102.8 mg ginseng 61.7 mg curcumin 102.8 mg berberine |

*Doses of products were converted by allometric scaling, which takes into account differences in body surface area to calculate equivalent doses for rat by the following calculation, assuming an 60 kg human: RD = HD(g)/60 kg*6.17 (For example: (200 mg/60)*6.17 = 20.6 mg/kg BW); where RD is the rat dosage of products, HD is the human dosage of products, and 6.17 is the conversion factor to convert a human dosage to a rat dosage

TABLE 2

Ingredients of standard and high-fat diet (HFD) fed to rats

| Ingredients, % | Standard diet | HFD |
|---|---|---|
| Casein | 20.00 | 20.00 |
| Corn Starch | 57.95 | 15.00 |
| Sucrose | 5.00 | 14.95 |
| Vegetable oil | 7.00 | — |
| Beef tallow | — | 40.00 |
| Cellulose | 5.00 | 5.00 |
| Mineral premix* | 3.50 | 3.50 |
| Vitamin premix** | 1.00 | 1.00 |
| L-cysteine | 0.30 | 0.30 |
| Choline bitartrate | 0.25 | 0.25 |

*Modified AIN-93G-MX
**AIN-93-VX (No: 310025)

Rats will be offered ad libitum chow or chocolate. Every day one of five different variants of commercially available chocolate bars will be offered ad libitum along with ad libitum chow. The composition of the different chocolate bars will have energy content around 2300 KJ/100 g, sugars 50-60 g/100 g and fat 30-40 g/100 g. Chow will be placed in the lid of the cage and chocolate will be placed inside the cage. To encourage a large energy intake in the rats, the five different kinds of chocolate bars will be offered with daily alternation. It is expected that the rats will prefer eating the chocolate, resulting in more than 90% of calories being consumed as chocolate. Treatment will be initiated after 1-3 months period of chow/chocolate diet. The treatment duration will be 12 weeks. Rats will be dosed with study products by oral gavage, which will be administered daily.

Body weight and food intake will be measured manually on a daily basis during the treatment period. Caloric efficiency (kcal/g body weight gain) will be calculated daily by multiplying food intake (g) by the caloric content of the diet and dividing this result by daily body weight gain (g). Delta body weight gain will be calculated by subtracting the body weight of the rat the day of the metabolic test from that of the first day of the experiment. The daily body gain will be calculated by taking body weight gain and dividing by the number of days between the start of the experiment and the day of the metabolic test. Following the study, rats will be sacrificed.

Visceral fat will be removed from the carcass and weighed. Blood samples will be collected by gel biochemical tubes and serum samples will be taken and centrifuged at 4° C. at 3000×g for 10 min in a chilled centrifuge. Tissues obtained from the animals will be stored in a deep freeze at −80° C. until analysis.

Serum glucose, triglycerides, cholesterol, aspartate aminotransferase (AST), alanine aminotransferase (ALT), urea, and creatinine levels will be analyzed with a portable automated chemistry analyzer (Samsung LABGEO PT10, Samsung Electronics Co., Suwon, Korea). Concentrations of serum insulin, leptin and free fatty acids will be measured with rat-specific kits (Cayman Chemical Co., Ann Arbor, MI, USA) by enzyme-linked immunosorbent assay (ELISA, Elx-800, Bio-Tek Instruments Inc, Vermont, USA). Concentrations of GLP-1 (7-36) amide levels will be measured using the relevant commercial kits by ELISA (Elx-800, Bio-Tek Instruments Inc, Vermont, USA) method. Concentrations of active ghrelin will be measured using an RIA kit (Ghrelin Active RIA kit; Linco Research).

The rats' brains will be immediately excised, flushed with ice-cold saline, immersed in liquid nitrogen, and stored at −80° C. Reverse transcription polymerase chain reaction and western blot will be performed to determine levels of whole-brain GLP-1R, c-Fos, prolactin-releasing peptide (PrRP) and tyrosine hydroxylase. Special attention will be given to the hindbrain for c-Fos activation in the area of the Nucleus Tractus Solitarius, Dorsal Vagal Complex and Area Postrema as these are known brain areas for GLP-1 activity.

Segments of cecum and colon (proximal, medial, distal colon, corresponding to 2-cm segments taken just after the cecal junction, in the middle of the colon, and just before the rectum, respectively) will be immediately excised, flushed with ice-cold saline, immersed in liquid nitrogen, and stored at −80° C. for further western blot analysis. Full and empty cecum, liver, and epidydimal fat pads will be weighed.

Liver samples will be clamped immediately in liquid nitrogen. Liver triglyceride levels will be measured using the relevant commercial kits by ELISA.

Proximal colon and cecum mRNA, GLP-1, and GLP-2 levels will be determined by Reverse Transcriptase (RT)-Polymerase Chain Reaction (PCR).

The following markers will be measured by western blot in tissues: intestinal insulin receptor substrate, GLP-1 (7-36) amide, and GLP-2 levels.

All quantitative data will be presented as mean±standard deviation (SD). Experimental values will be analyzed by one-way ANOVA. A value of $p<0.05$ will be considered to be statistically significant. All analyses will be performed using Statistical Analysis Software (SPSS 17.0).

Example 4

One or more formulations intended for oral administration, e.g., a powder, a granule, a capsule (soft, hard, gel, or plant-based), a pill, a tablet, a caplet, etc., (i) comprising an amount of at least one GLP-1R agonist composition, as disclosed herein, (ii) comprising an amount of at least one DPP-4 inhibitor composition, as disclosed herein, and/or (iii) comprising an amount of at least one GLP-1R agonist composition and an amount of at least one DPP-4 inhibitor composition, as disclosed herein, will be prepared via methods disclosed herein, or via methods known in the art. In the aforementioned formulations, individual batches of a single formulation, e.g. an oral formulation comprising an amount of at least one GLP-1R agonist composition and an amount of at least one DPP-4 inhibitor composition, will be split into two sub-batches: (i) the formulation, as prepared, and (ii) the formulation prepared with a coating that can delay/control release or enable sustained release of one or more active ingredients from the formulation, i.e., the GLP-1R agonist(s) and/or DPP-4 inhibitors(s), by coating the surface of the formulation with a slow dissolving coating, a pH-responsive coating, an enteric coating, etc.

Release of GLP-1R agonist(s) and/or DPP-4 inhibitors(s) from the oral formulations will be evaluated by placing the oral formulations in a large volume of physiological-mimetic liquid, e.g. phosphate buffered saline, having a pH that is within a normal physiological range of the site where release of the GLP-1R agonist(s) and/or DPP-4 inhibitors(s) is desired, e.g. a pH of about 1.5-4 for release in the stomach, a pH of about 5.6-8.0 for release in the duodenum, a pH of 7.2-8.5 for release in the GI tract, etc. Aliquots from the physiological-mimetic liquid will be withdrawn at predetermined time points. The amount of GLP-1R agonist(s) and/or DPP-4 inhibitors(s) in an aliquot will be characterized using an appropriate method, e.g., UV-vis spectroscopy, a colorimetric assay, mass spectrometry, etc.

Release profiles will be generated by plotting the amount of GLP-1R agonist(s) and/or DPP-4 inhibitors(s) released vs. the time at which an aliquot was withdrawn.

Example 5

In vivo experiments in accordance with Example 3 will be performed using the formulations evaluated in Example 4, and will assess the same endpoints of Example 3, i.e., weight loss/gain and biomarker levels.

In vivo experiments will be performed to determine at least the following: (i) the effect of a formulation comprising an amount of at least one GLP-1R agonist composition on the endpoints; (ii) the effect of a formulation comprising an amount of at least one GLP-1R agonist composition on the endpoints; (iii) the effect of a formulation comprising an amount of at least one GLP-1R agonist composition and an amount of at least one DPP-4 inhibitor composition on the endpoints; (iv) the effect of concurrently administering (i) and (ii) on the endpoints; (v) the effect of administering (i) and (ii) at separate times on the end points—i.e., administering (ii) prior to (i) or administering (i) prior to (ii), wherein the first formulation is administered, for example, 0.5, 1, 2, 4, 8 hrs prior to the second formulation; (vi) the effect of administering any of (i)-(v) at a time prior to a meal on the endpoints—for example, 0.5, 1, 2, 4, 8 hrs prior to the meal; (vii) the effect of administering any of (i)-(v) at a time after a meal on the endpoints—for example, 0.5, 1, 2, 4, 8 hrs after to the meal; and (viii) the effect of administering (v), wherein one formulation is administered prior to a meal and one formulation is administered after the meal—for example, the first formulation being administered, for example, 0.5, 1, 2, 4, 8 hrs before the meal and the second formulation being administered, for example, 0.5, 1, 2, 4, 8 hrs after to the meal.

Example 6

A clinical trial will be performed to evaluate the efficacy of the most effective formulations, dosing regimens, and dosing scheduled determined from the in vivo work of Example 5.

As a primary outcome, the clinical trial will assess weight loss/lack of weight gain in the subjects evaluated compared to placebo and commercially available formulations.

As secondary outcomes, the clinical trial will assess serum levels of glucose, triglycerides, cholesterol, aspartate aminotransferase (AST), alanine aminotransferase (ALT), urea, creatinine, GLP-1, and the like.

The clinical trial will confirm that the formulations disclosed herein improve at least one endpoint set forth in the primary and/or secondary outcomes compared to the placebo and comparative arms. The clinical trial will also confirm that the formulations disclosed herein pose no significant adverse safety outcome compared to the placebo arm.

While exemplary embodiments, aspects and variations have been provided herein, those of skill in the art will recognize certain modifications, permutations, additions and combinations and certain sub-combinations of the embodiments, aspects, and variations. It is intended that the following claims are interpreted to include all such modifications, permutations, additions and combinations and certain sub-combinations of the embodiments, aspects and variations are within their scope.

The invention claimed is:

1. A granule, soft capsule, hard capsule, gel capsule, plant based capsule, sachet, pill, tablet, caplet, gum, or dissolvable oral strip comprising a synergistic amount of Uva ursi extract and pterostilibene, wherein the ratio of the Uva ursi extract to the pterostilbene is 2.5:1 to 1:6.

2. The granule, soft capsule, hard capsule, gel capsule, plant based capsule, sachet, pill, tablet, caplet, gum, or dissolvable oral strip of claim 1, further comprising a component selected from the group consisting of ginseng, curcumin, GLP-1, conjugated linoleic acid, bayberry powder, berberine, berberine hydrochloride, camellia sinensis, capsaicin, dong quai root powder, epigallocatechin gallate, freeze dried kefir milk, garcinia cambogia, hydroxycitric acid, lion's mane mushroom, medium chain triglycerides, quercetin, resveratrol, sucralose and combinations thereof.

3. The granule, soft capsule, hard capsule, gel capsule, plant based capsule, sachet, pill, tablet, caplet, gum, or dissolvable oral strip of claim 1, further comprising ginseng.

4. The granule, soft capsule, hard capsule, gel capsule, plant based capsule, sachet, pill, tablet, caplet, gum, or dissolvable oral strip of claim 1, further comprising curcumin.

5. The granule, soft capsule, hard capsule, gel capsule, plant based capsule, sachet, pill, tablet, caplet, gum, or dissolvable oral strip of claim 1, further comprising a mixture of a ginseng and curcumin.

6. The granule, soft capsule, hard capsule, gel capsule, plant based capsule, sachet, pill, tablet, caplet, gum, or dissolvable oral strip of claim 1, further comprising a component selected from the group consisting of climacostol, desoxyrhapontigenin, dihydropinosylvin monomethyl ether, dihydroresveratrol, gnetol, isorhapontigenin, isoresveratrol, oxyresveratrol, piceatannol, pinostilbene, pinosylvin, pinosylvin monomethyl ether, resveratrol, rhaponti-genin, triacetylresveratrol, trimethylresveratrol, 3'-hydroxypterostilbene, 3,4'-dimethoxy resveratrol, 3,5-di-hydroxy-4-ethyl-trans-stilbene, 3,5-dihydroxy-4-isopropyl-stilbene, 4'-bromo-resveratrol, 4,4'-dihydroxystilbene, allocryptopine, berberine, canadine, columbamine, coptisine, cordylamine, corysamine, cryptopine, cyclanoline, dihyd-roberberine, dihydrocoptisine, dihydropalmatine, epiberber-ine, groenlandicine, jatrorrhizine, methyl stepholidine, pal-matine, protopine, pseudoberberine, pseudocoptisine, scoulerine, stepharanine, stepholidine, stylopine, tetrahyd-roberberine, tetrahydropalmatine and combinations thereof.

7. The granule, soft capsule, hard capsule, gel capsule, plant based capsule, sachet, pill, tablet, caplet, gum, or dissolvable oral strip of claim 1, further comprising a component selected from the group consisting of resveratrol, berberine and combinations thereof.

8. The granule, soft capsule, hard capsule, gel capsule, plant based capsule, sachet, pill, tablet, caplet, gum, or dissolvable oral strip of claim 1, further comprising a component selected from the group consisting of ginseng, curcumin, resveratrol, berberine and combinations thereof.

9. The granule, soft capsule, hard capsule, gel capsule, plant based capsule, sachet, pill, tablet, caplet, gum, or dissolvable oral strip of claim 1, wherein the granule, soft capsule, hard capsule, gel capsule, plant based capsule, sachet, pill, tablet, caplet, gum, or dissolvable oral strip comprises a pH-responsive or enteric coating.

\* \* \* \* \*